US009789139B2

(12) United States Patent
Denaro et al.

(10) Patent No.: US 9,789,139 B2
(45) Date of Patent: Oct. 17, 2017

(54) GENE THERAPY VECTORS FOR ADRENOLEUKODYSTROPHY AND ADRENOMYELONEUROPATHY

(75) Inventors: Maria Joann Denaro, Marblehead, MA (US); Mitchell Howard Finer, Stow, MA (US); Gabor Veres, Medford, MA (US); Julian Down, Cambridge, MA (US)

(73) Assignee: bluebird bio, Inc., Cambridge, MA (US)

( * ) Notice: Subject to any disclaimer, the term of this patent is extended or adjusted under 35 U.S.C. 154(b) by 0 days.

(21) Appl. No.: 14/125,220

(22) PCT Filed: Jun. 8, 2012

(86) PCT No.: PCT/US2012/041639
§ 371 (c)(1),
(2), (4) Date: Oct. 3, 2014

(87) PCT Pub. No.: WO2012/170911
PCT Pub. Date: Dec. 13, 2012

(65) Prior Publication Data
US 2015/0037296 A1 Feb. 5, 2015

Related U.S. Application Data

(60) Provisional application No. 61/495,857, filed on Jun. 10, 2011.

(51) Int. Cl.
| | |
|---|---|
| *A61K 48/00* | (2006.01) |
| *A61K 38/17* | (2006.01) |
| *C12N 15/86* | (2006.01) |
| *C12N 5/071* | (2010.01) |
| *C12N 7/00* | (2006.01) |
| *A61K 35/51* | (2015.01) |
| *C07K 14/705* | (2006.01) |
| *A61K 35/28* | (2015.01) |

(52) U.S. Cl.
CPC ............ *A61K 35/51* (2013.01); *A61K 35/28* (2013.01); *A61K 38/177* (2013.01); *A61K 48/0058* (2013.01); *C07K 14/705* (2013.01); *C12N 5/0686* (2013.01); *C12N 7/00* (2013.01); *C12N 15/86* (2013.01); *A61K 48/005* (2013.01); *C12N 2740/15043* (2013.01); *C12N 2740/16043* (2013.01); *C12N 2800/24* (2013.01); *C12N 2830/00* (2013.01); *C12N 2830/008* (2013.01); *C12N 2830/50* (2013.01); *C12N 2830/60* (2013.01); *C12N 2840/00* (2013.01)

(58) Field of Classification Search
None
See application file for complete search history.

(56) References Cited

U.S. PATENT DOCUMENTS

| | | |
|---|---|---|
| 5,658,784 A | 8/1997 | Eckner et al. |
| 5,994,136 A | 11/1999 | Naldini et al. |
| 6,013,516 A | 1/2000 | Verma et al. |
| 6,133,454 A | 10/2000 | Lecouve et al. |
| 6,489,142 B1 | 12/2002 | Torrent et al. |
| 6,682,907 B1 | 1/2004 | Charneau et al. |
| 8,304,234 B2 | 11/2012 | Weiner et al. |
| 8,858,928 B2 | 10/2014 | Denaro et al. |
| 9,061,031 B2 | 6/2015 | Denaro et al. |
| 2007/0048285 A1 | 3/2007 | Baum et al. |
| 2011/0027310 A1 | 2/2011 | Medin et al. |
| 2013/0004471 A1 | 1/2013 | Denaro et al. |
| 2015/0064150 A1 | 3/2015 | Denaro et al. |

FOREIGN PATENT DOCUMENTS

| | | |
|---|---|---|
| EP | 2020444 A1 | 2/2009 |
| JP | 2002-539758 | 11/2002 |
| JP | 2007-54069 | 3/2007 |
| JP | 2008-538174 | 10/2008 |
| WO | WO 99/14310 A1 | 3/1999 |
| WO | WO 02/87341 A1 | 11/2002 |
| WO | WO 2004/054512 A2 | 7/2004 |
| WO | WO 2006/089001 A2 | 8/2006 |
| WO | WO 2007/104633 A1 | 9/2007 |
| WO | WO 2010/105251 A2 | 9/2010 |

OTHER PUBLICATIONS

Matsuzaka, et al. (2012) "Elovl6 promotes nonalcoholic steatohepatitis", Hepatology, 56(6): 2199-208, Abstract Only.*
Cartier, et al. (2009) "Hematopoietic Stem Cell Gene Therapy with a Lentiviral Vector in X-Linked Adrenoleukodystrophy", Science, 2326, 818-23.*
Nadig (2009) "Stem cell therapy—Hype or Hope? A review", Journal of Conservative Dentistry, 12(4): 131-38 (printed from PMC online version: 11 pages long).*
Alt and Caselmann. "Liver-directed gene therapy: molecular tools and current preclinical and clinical studies", *Journal of Hepatology* (1995), 23:746-58.
Atweh et al., "Hemoglobinopathies," Hematology, Am. Soc. Hematol. (2003), pp. 14-39.
Balcaitis, et al., "Lentiviral Transduction of Microglial Cells", *Glia* (2005), 50(1): 48-55.
Bell, A.C. et al., 2001, Geneseq Accession No. AAF67644, computer printout p. 5-6.
Bell, A.C. et al., "The Protein CTCF is Required for the Enhancer Blocking Activity of Vertebrate Insulators," *Cell* (1999), 98:387-396.

(Continued)

*Primary Examiner* — Robert M Kelly
(74) *Attorney, Agent, or Firm* — Cooley LLP

(57) ABSTRACT

The present invention provides compositions comprising retroviral vectors, transduced cells, and methods of using the same for gene therapy. In particular, the present invention relates to lentiviral vectors and cells transduced with those vectors to provide gene therapy to subjects having an adrenoleukodystrophy and/or adrenomyeloneuropathy.

14 Claims, 13 Drawing Sheets

(56) References Cited

OTHER PUBLICATIONS

Biffi, Alessandra et al., "Gene therapy for leukodystrophies", *Human Molecular Genetics* (2011), 20(1): R42-R53, 12 pages. [Advance Access published on Mar. 31, 2011].
Brody and Crystal, "Adenovirus-mediated in vivo gene transfer", *Ann. N. Y Acad. Sci.* (1994), 716:90-101; discussion 101-3.
Cartier, et al. "Lentiviral Hematopoietic Cell Gene Therapy for X-Linked Adrenoleukodystrophy", *Methods in Enzymology* (2012), 507(10) 187-198.
Cartier, et al., "Hematopoietic Stem Cell Transplantation and Hematopoietic Stem Cell Gene Therapy in X-Linked Adrenoleukodystrophy", *Brain Pathology* (2010), 20(4): 857-862.
Challita, P.M. et al., "Multiple modifications in cis elements of the long terminal repeat of retroviral vectors lead to increased expression and decreased DNA methylation in embryonic carcinoma cells", *Journal of Virology* (1995), 69(2):748-55.
Chung, J.H. et al., "A 5' Element of the Chicken beta-Globin Domain Serves as an Insulator in Human Erythroid Cells and Protects against Position Effect in Drosphila," *Cell* (1993), 74:505-514.
Chung, J.H. et al., "Characterization of the chicken beta-globin insulator", *Proc. Natl. Acad. Sci. USA* (1997), 94: 575-580.
Cullen and Greene, "Regulatory Pathways Governing HIV-1 Replication", *Cell* (1989), 58:423-426.
Cullen, B.R., "Human Immunodeficiency Virus as a Prototypic Complex Retrovirus", *Journal of Virology* (1991), 65(3): 1053-1056.
Desheng, Yao, "Construction of the lentiviral expression plasmid carrying OPCML gene", *Prog Obstet Gyneco*, published on Jul. 31, 2006 (with English Abstract).
Dull et al., "A third-generation lentivirus vector with a conditional packaging system", *Journal of Virology* (1998), 72(11):8463-8671.
Ferry and Heard, "Liver-Directed Gene Transfer Vectors", *Human Gene Therapy* (1998), 9:1975-81.
Higashimoto, et al., "The woodchuck hepatitis virus post-transcriptional regulatory element reduces readthrough transcription from retroviral vectors", *Gene Therapy* (2007), 14: 1298-1304.
Hlavaty, et al., "Effect of posttranscriptional regulatory elements on transgene expression and virus production in the context of retroviral vectors", *Virology* (2005), 341: 1-11.
Huang and Yen, "Role of the hepatitis B virus posttranscriptional regulatory element in export of intronless transcripts", *Molecular and Cellular Biology* (1995), 15(7):3864-3869.
Huang and Flint, "The Tripartite Leader Sequence of Subgroup C Adenovirus Major Late mRNAs Can Increase the Efficiency of mRNA Export", *Journal of Virology* (1998), 72(1): 225-235.
Kay, M.A., "Adenoviral Vectors for Hepatic Gene Transfer in Animals", *Chest* (1997), 111:138S-142S.
Klein et al., "WPRE-mediated enhancement of gene expression is promoter and cell line specific", *Gene* (2006), 372: 153-161.
Kozak, M., "Point mutations define a sequence flanking the AUG initiator codon that modulates translation by eukaryotic ribosomes", *Cell* (1986), 44(2):283-92.
Kozak, M., "An analysis of 5'-noncoding sequences from 699 vertebrate messenger RNAs", *Nucleic Acids Res.* (1987), 15(20):8125-48.
Kumar and Woon-Khiong, "Optimization of Lentiviral Vectors Generation for Biomedical and Clinical Research Purposes: Contemporary Trends in Technology Development and Applications", *Current Gene Therapy* (2011), 11(2): 144-153.
Lee, H. C. et al., "Remission in models of type 1 diabetes by gene therapy using a single-chain insulin analogue", *Nature* (2000), 408(6811): 483-488.
Liu and Mertz, "HnRNP L binds a cis-acting RNA sequence element that enables intron-dependent gene expression", *Genes & Development* (1995), 9: 1766-1780.

Naldini L. et al., "Efficient transfer, integration, and sustained long-term expression of the transgene in adult rat brains injected with a lentiviral vector", *Proc. Natl. Acad. Sci. USA* (1996), 93(21): 11382-11388.
Naldini, L. et al., "In vivo gene delivery and stable transduction of nondividing cells by a lentiviral vector", *Science*(1996), 272(5259): 263-267.
Naldini, L., "Lentiviruses as gene transfer agents for delivery to non-dividing cells", *Curr Opin Biotechnol.* (1998), 5: 457-63.
Nau, Jean-Yves, "Une thérapie génique contre l'adrenoleucodystrophie", *Rev Med Suisse* (2009), Retrieved from the Internet: URL:http:jjrms.medhyg.chjnumero-226-page-2363.htm, [retrieved on Nov. 21, 2014], the whole document.
Oka, K. et al., "Recent advances in liver-directed gene therapy: implications for the treatment of dyslipidemia", *Current Opinion in Lipidology* (2000), 11:179-86.
Payen et al., "First human gene therapy trial for haemoglobin disorders," Chapter 15, *Disorders of Erythropoiesis, Erythrocytes and Iron Metabolism*, The Handbook 2009 Edition, pp. 390-401, 2009.
PCT/US2012/041693, International Search Report mailed Feb. 13, 2013.
PCT/US2012/041693, Written Opinion mailed Feb. 13, 2013.
PCT/US2012/041693, International Preliminary Report on Patentability mailed Dec. 10, 2013.
Rothe et al., "Biosafety Challenges for Use of Lentiviral Vectors in Gene Therapy", *Current Gene Therapy* (2013), 13(6): 453-468.
Schwenter, et al., "Optimization of human erythropoietin secretion from MLV-infected human primary fibroblasts used for encapsulated cell therapy", *Journal of Gene Medicine* (2003), 5(3): 246-57.
Shiratori, Y. et al., "Strategy of liver-directed gene therapy: present status and. future prospects", *Liver* (1999), 19: 265-274.
Skolnick and Fetrow, "From genes to protein structure and function: novel applications of computational approaches in the genomic era", *Trends in Biotech* (2000), 18: 34-39.
Smith-Arica and Bartlett, "Gene Therapy: Recombinant Adeno-associated Virus Vectors", *Curr. Cardiol. Rep.* (2001), 3:43-49.
Strayer, D.S., "Viral gene delivery", *Expert Opinion on Investigational Drugs* (1999), 8(12): 2159-2172.
Thulé and Liu, "Regulated hepatic insulin gene therapy of STZ-diabetic rats", *Gene Therapy* (2000), 7: 1744-1752.
Yang, N.S., "Gene Transfer into Mammalian Somatic Cells in Vivo", *Critical Reviews in Biotechnology* (1992), 12(4): 335-356.
Zennou, et al., "HIV-1 Genome Nuclear Import Is Mediated by a Central DNA Flap", *Cell* (2000), 101: 173-185.
Zufferey et al., "Woodchuck hepatitis virus posttranscriptional regulatory element enhances expression of transgenes delivered by retroviral vectors", *J Virol.* (1999), 73(4):2886-92.
Zufferey et al., "Multiply attenuated lentiviral vector achieves efficient gene delivery in vivo", *Nat Biotechnol.* (1997), 15(9): 871-875.
European Application No. 12796252.0, Extended European Search Report dated Dec. 5, 2014, 8 pages.
U.S. Appl. No. 13/492,553, Non Final Office Action mailed Aug. 6, 2013, 11 pages.
U.S. Appl. No. 13/492,553, Final Office Action mailed Nov. 8, 2013, 14 pages.
U.S. Appl. No. 13/492,553, Advisory Action mailed May 2, 2014, 14 pages.
U.S. Appl. No. 13/492,553, Non Final Office Action mailed Jun. 5, 2014, 17 pages.
U.S. Appl. No. 13/492,553, Notice of Allowance mailed Sep. 8, 2014, 17 pages.
U.S. Appl. No. 14/488,058, Office Action dated Dec. 18, 2014, 10 pages.
U.S. Appl. No. 14/488,058, Notice of Allowance dated Apr. 30, 2015, 7 pages.
Schambach, et al., "Improving Transcriptional Termination of Self-inactivating Gamma-retroviral and Lentiviral Vectors," Molecular Therapy, 15(6)1167-1173, 2007.

\* cited by examiner

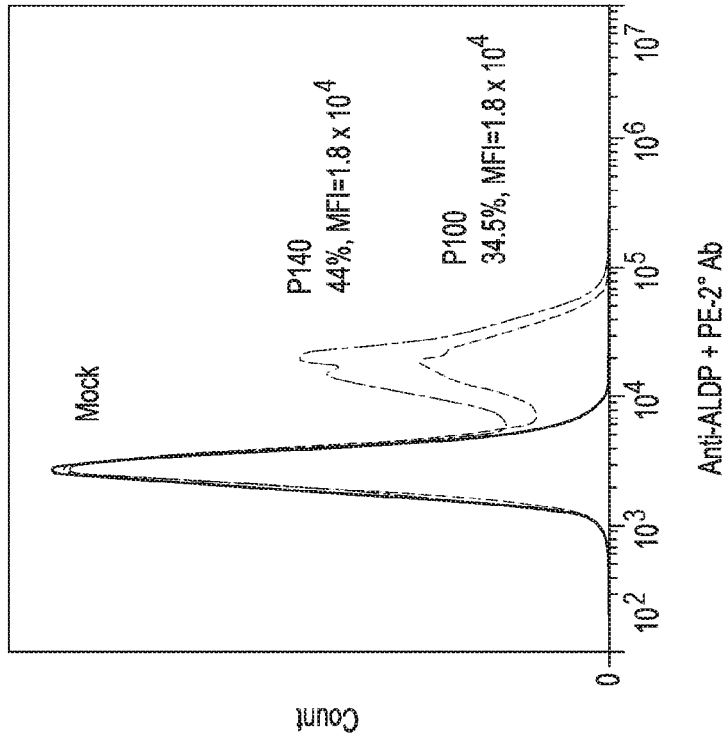
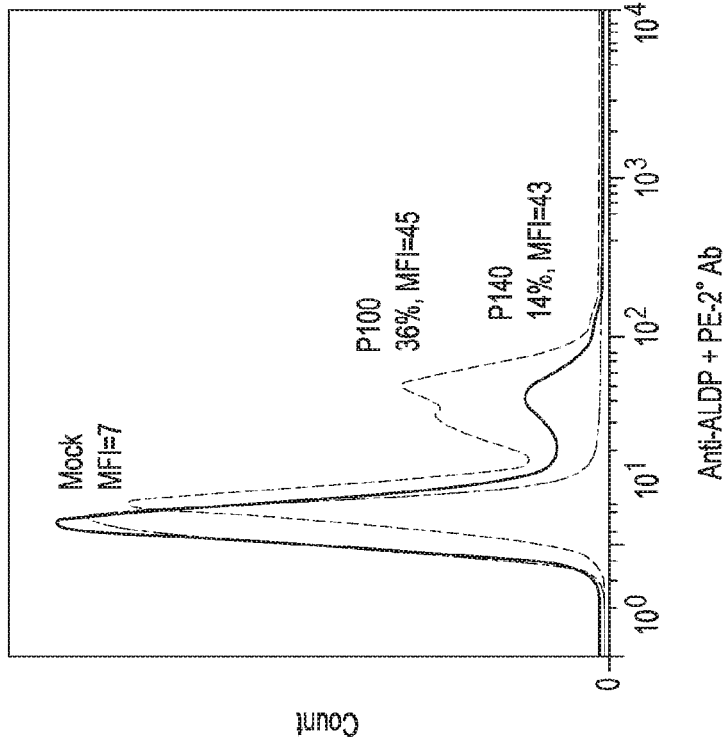
FIG. 8A1

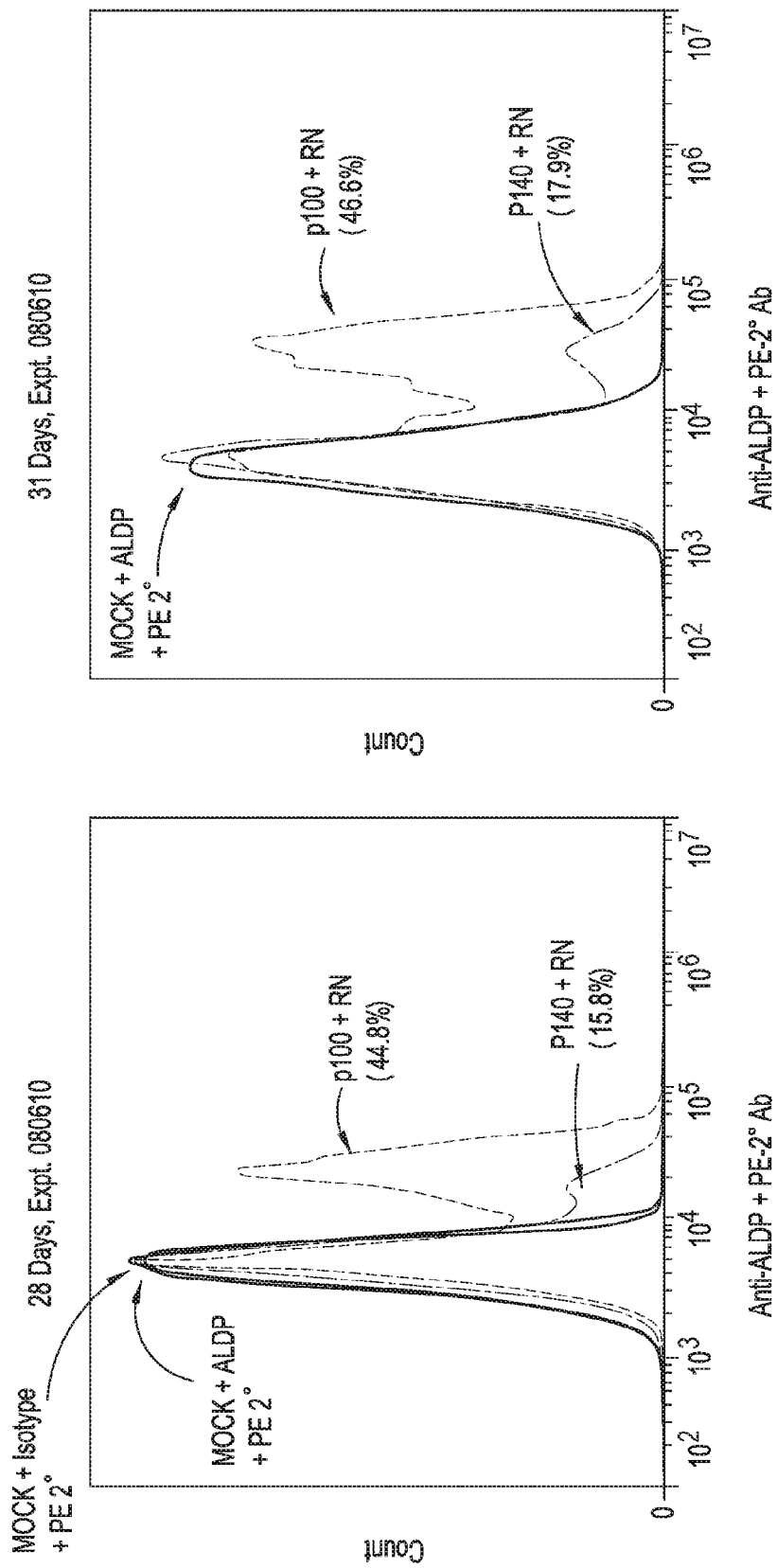
FIG. 8A2

SEQUENCE LISTING

<160> NUMBER OF SEQ ID NOS: 3

<210> SEQ ID NO 1
<211> LENGTH: 2297
<212> TYPE: DNA
<213> ORGANISM: Homo sapiens

<400> SEQUENCE: 1

```
ccagcccag tccctacgcg gcagccagcc caggtgacat gccggtgctc tccaggcccc      60
ggccctggcg ggggaacacg ctgaagcgca cggccgtgct cctggccctc gcggcctatg     120
gagcccacaa agtctacccc ttggtgcgcc agtgcctggc cccggccagg ggtcttcagg     180
cgcccgccgg ggagcccacg caggaggcct ccggggtcgc ggcggccaaa gctggcatga     240
accgggtatt cctgcagcgg ctcctgtggc tcctgcggct gctgttcccc cgggtcctgt     300
gccgggagac ggggctgctg gccctgcact cggccgcctt ggtgagccgc accttcctgt     360
cggtgtatgt ggcccgcctg gacggaaggc tggcccgctg catcgtccgc aaggacccgc     420
gggcttttgg ctggcagctg ctgcagtggc tcctcatcgc cctccctgct accttcgtca     480
acagtgccat ccgttacctg gagggccaac tggccctgtc gttccgcagc cgtctggtgg     540
cccacgccta ccgcctctac ttctcccagc agacctacta ccgggtcagc aacatggacg     600
ggcggcttcg caaccctgac cagtctctga cggaggacgt ggtggccttt gcggcctctg     660
tggcccacct ctactccaac ctgaccaagc cactcctgga cgtggctgtg acttcctaca     720
ccctgcttcg ggcggcccgc tcccgtggag ccggcacagc ctggccctcg gccatcgccg     780
gcctcgtggt gttcctcacg gccaacgtgc tgcgggcctt ctcgcccaag ttcggggagc     840
tggtggcaga ggaggcgcgg cggaaggggg agctgcgcta catgcactcg cgtgtggtgg     900
ccaactcgga ggagatcgcc ttctatgggc gccatgaggt ggagctggcc ctgctacagc     960
gctcctacca ggacctggcc tcgcagatca acctcatcct tctggaacgc ctgtggtatg    1020
```

```
ttatgctgga gcagttcctc atgaagtatg tgtggagcgc ctcgggcctg ctcatggtgg    1080
ctgtccccat catcactgcc actggctact cagagtcaga tgcagaggcc gtgaagaagg    1140
cagccttgga aaagaaggag gaggagctgg tgagcgagcg cacagaagcc ttcactattg    1200
cccgcaacct cctgacagcg gctgcagatg ccattgagcg gatcatgtcg tcgtacaagg    1260
aggtgacgga gctggctggc tacacagccc gggtgcacga gatgttccag gtatttgaag    1320
atgttcagcg ctgtcacttc aagaggccca gggagctaga ggacgctcag gcggggtctg    1380
ggaccatagg ccggtctggt gtccgtgtgg agggcccccct gaagatccga ggccaggtgg    1440
tggatgtgga cagggggatc atctgcgaga acatccccat cgtcacgccc tcaggagagg    1500
tggtggtggc cagcctcaac atcagggtgg aggaaggcat gcatctgctc atcacaggcc    1560
ccaatggctg cggcaagagc tccctgttcc ggatcctggg tgggctctgg cccacgtacg    1620
gtggtgtgct ctacaagccc ccaccccagc gcatgttcta catcccgcag aggccctaca    1680
tgtctgtggg ctccctgcgt gaccaggtga tctacccgga tcagtggag gacatgcaaa    1740 ggaagggcta ctcggagcag gacctggaag ccatcctgga cgtcgtgcac ctgcaccaca    1800
tcctgcagcg ggagggaggt tgggaggcta tgtgtgactg gaaggacgtc ctgtcgggtg    1860
gcgagaagca gagaatcggc atggcccgca tgttctacca caggcccaag tacgccctcc    1920 tgatgaatg caccagcgcc gtgagcatcg acgtggaagg caagatcttc caggcggcca    1980
aggacgcggg cattgccctg ctctccatca cccaccggcc ctccctgtgg aaataccaca    2040
cacacttgct acagttcgat ggggagggcg gctggaagtt cgagaagctg gactcagctg    2100
cccgcctgag cctgacggag gagaagcagc ggctggagca gcagctggcg ggcattccca    2160
agatgcagcg gcgcctccag gagctctgcc agatcctggg cgaggccgtg gccccagcgc    2220
atgtgccggc acctagcccg caaggccctg gtggcctcca gggtgcctcc acctgactcg    2280 aggggggggcc cggtacc                                                  2297

<210> SEQ ID NO 2
<211> LENGTH: 2238
<212> TYPE: DNA
<213> ORGANISM: Homo sapiens

<400> SEQUENCE: 2
atgccggtgc tctccaggcc ccggccctgg cgggggaaca cgctgaagcg cacggccgtg      60
ctcctggccc tcgcggccta tggagcccac aaagtctacc ccttggtgcg ccagtgcctg     120
gccccggcca ggggtcttca gcgcccgcc ggggagccca cgcaggaggc ctccggggtc     180
gcggcggcca agctggcat gaaccgggta ttcctgcagc ggctcctgtg ctcctgcgg     240 ctgctgttcc ccgggtcct gtgccggag acggggctgc tggccctgca ctcggccgcc     300
ttggtgagcc gcaccttcct gtcggtgtat gtggcccgcc tggacggaag gctggcccgc     360
tgcatcgtcc gcaaggaccc gcgggctttt ggctggcagc tgctgcagtg gctcctcatc     420
gccctccctg ctaccttcgt caacagtgcc atccgttacc tggagggcca actggccctg     480
tcgttccgca gccgtctggt ggcccacgcc taccgcctct acttctccca gcagacctac     540
taccgggtca gcaacatgga cggcggcttc gcaaccctg accagtctct gacgaggac     600 gtggtggcct ttgcggcctc tgtgcccac ctctactcca acctgaccaa gccactcctg     660
gacgtggctg tgacttccta cacctgcttt cggcgccccc gctcccgtgg agccggcaca     720
gcctggccct cggccatcgc cggcctcgtg gtgttcctca cggccaacgt gctgcgggcc     780
```

```
ttctcgccca agttcgggga gctggtggca gaggaggcgc ggcggaaggg ggagctgcgc        840
tacatgcact cgcgtgtggt ggccaactcg gaggagatcg ccttctatgg gggccatgag        900
gtggagctgg ccctgctaca gcgctcctac caggacctgg cctcgcagat caacctcatc        960
cttctggaac gcctgtggta tgttatgctg gagcagttcc tcatgaagta tgtgtggagc       1020
gcctcgggcc tgctcatggt ggctgtcccc atcatcactg ccactggcta ctcagagtca       1080
gatgcagagg ccgtgaagaa ggcagccttg gaaaagaagg aggaggagct ggtgagcgag       1140
cgcacagaag ccttcactat tgcccgcaac ctcctgacag cggctgcaga tgccattgag       1200
cggatcatgt cgtcgtacaa ggaggtgacg gagctggctg gctacacagc ccgggtgcac       1260
gagatgttcc aggtatttga agatgttcag cgctgtcact tcaagaggcc cagggagcta       1320
gaggacgctc aggcggggtc tgggaccata ggccggtctg gtgtccgtgt ggagggcccc       1380
ctgaagatcc gaggccaggt ggtggatgtg gaacagggga tcatctgcga aacatcccc       1440 atcgtcacgc cctcaggaga ggtggtggtg gccagcctca acatcagggt ggaggaaggc       1500
atgcatctgc tcatcacagg ccccaatggc tgcggcaaga gctccctgtt ccggatcctg       1560
ggtgggctct ggcccacgta cggtggtgtg ctctacaagc ccccacccca gcgcatgttc       1620
tacatcccgc agaggcccta catgtctgtg ggctccctgc gtgaccaggt gatctacccg       1680
gactcagtgg aggacatgca aaggaagggc tactcggagc aggacctgga agccatcctg       1740
gacgtcgtgc acctgcacca catcctgcag cgggagggag gttgggaggc tatgtgtgac       1800
tggaaggacg tcctgtcggg tggcgagaag cagagaatcg gcatggcccg catgttctac       1860
cacaggccca agtacgccct cctggatgaa tgcaccagcg ccgtgagcat cgacgtggaa       1920
ggcaagatct ccaggcggc caaggacgcg ggcattgccc tgctctccat cacccaccgg       1980
ccctccctgt ggaaatacca cacacacttg ctacagttcg atggggaggg cggctggaag       2040
ttcgagaagc tggactcagc tgcccgcctg agcctgacgg aggagaagca gcggctggag       2100
cagcagctgg cgggcattcc caagatgcag cggcgcctcc aggagctctg ccagatcctg       2160
ggcgaggccg tggccccagc gcatgtgccg gcacctagcc cgcaaggccc tggtggcctc       2220
cagggtgcct ccacctga                                                    2238
```

<210> SEQ ID NO 3
<211> LENGTH: 399
<212> TYPE: DNA
<213> ORGANISM: Artificial Sequence
<220> FEATURE:
<223> OTHER INFORMATION: a MND promoter sequence
<400> SEQUENCE: 3

```
tttatttagt ctccagaaaa aggggggaat gaaagacccc acctgtaggt ttggcaagct         60
aggatcaagg ttaggaacag agagacagca gaatatgggc caaacaggat atctgtggta        120
agcagttcct gccccggctc agggccaaga acagttggaa cagcagaata tgggccaaac        180
aggatatctg tggtaagcag ttcctgcccc ggctcagggc caagaacaga tggtccccag        240
atgcggtccc gccctcagca gtttctagag aaccatcaga tgtttccagg gtgccccaag        300
gacctgaaat gaccctgtgc cttatttgaa ctaaccaatc agttcgcttc tcgcttctgt        360
tcgcgcgctt ctgctccccg agctcaataa aagagccca                              399
```

GENE THERAPY VECTORS FOR ADRENOLEUKODYSTROPHY AND ADRENOMYELONEUROPATHY

CROSS REFERENCE TO RELATED APPLICATIONS

This application is a U.S. national phase of PCT/US2012/041693, filed Jun. 8, 2012, which application claims the benefit under 35 U.S.C. §119(e) of U.S. Provisional Application No. 61/495,857, filed Jun. 10, 2011, which are incorporated by reference herein in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_003_01US_ST25.txt. The text file is 8 KB, was created on Dec. 10, 2013, and is being submitted electronically via EFS-Web, concurrent with the filing of the specification.

BACKGROUND

Technical Field

The present invention generally relates to gene therapy vectors. In particular, the present invention relates to lentiviral vectors that provide gene therapy for adrenoleukodystrophy and adrenomyeloneuropathy.

Description of the Related Art

Childhood cerebral adrenoleukodystrophy (CCALD) is a very rare, sometimes rapidly progressive, x-linked genetic neurologic disorder in boys (median age of onset age 7; range 3-15 years) that, untreated, leads to a vegetative state, and ultimately death, within a median of 5 years after diagnosis.

CCALD often initially presents as Addison's disease, but the diagnosis is usually made based on "sudden" decreases in attention, thinking, concentration, and other cerebral functions with confirmatory findings of cerebral demyelination on magnetic resonance imaging (MRI). Prior to demyelination, the MRI of the patient's brain is normal, and there are no neurodevelopmental abnormalities. The clinical course may be "slow" at first, but can become rapidly progressive and irreversible with the widespread loss of myelin in the brain. The terms "slow" and "sudden" are relative in that the duration of demyelination is not truly known, but the rapid decrease in cognitive and motor function can happen at any time and for unknown reasons. Indeed, the MRI changes precede symptoms, and can be floridly abnormal with widespread demyelination at a time when there are very few clinical manifestations of the disease. The incidence of x-linked adrenoleukodystrophy (ALD) in the United States is about 1:21,000 male births with about 35% developing CCALD; about 35 to 40 boys are diagnosed with CCALD each year. The cause of the disease is a mutation of the ATP-binding cassette, sub-family D (ALD), member 1 (ABCD1) gene leading to a dysfunctional or absent adrenoleukodystrophy protein (ALDP) gene product. ALDP localizes to cellular peroxisomes, where it participates in the degradation of very long chain fatty acids (VLCFA) (chain lengths of >20 carbons) to shorter fatty acids, which are used to maintain cellular structure and function.

The pathophysiology of the central nervous system (CNS) manifestations of CCALD is not well understood, but demyelination arises due to a local accumulation of VLCFA that cannot be metabolized because the defective ALDP does not support that process in the brain microglia. The rapidly progressive phase of the disease is caused by inflammation, possibly caused by acylation of cellular proteins by the VLCFA, which increases the loss of myelin. The rapidly progressive phase of CCALD can result in a boy deteriorating from normal function to severely disabled within months.

The only available treatment is allogeneic hematopoietic stem cell transplant (HCT) to supply cells that produce functional ALDP. Since the brain microglia are derived from the bone marrow, fully matched related donor human stem cell transplantation using cells producing functional ALDP can potentially ameliorate or stop the progression of demyelination. However, because it takes 12 to 18 months for allogeneic HCT to stabilize the disease, and because of the progressive nature of the disease, transplantation should be done as soon as possible upon diagnosis. This is sometimes problematic because of the lead times needed to find related or unrelated matched bone marrow stem cell donors. The use of allogeneic stem cells also presents a risk of graft failure and the development of acute and chronic graft versus host disease (GvHD). These complications can lead to death and are increased in incidence when unrelated donors are utilized as a source for allogeneic hematopoietic stem cells.

Another source of ALDP replacement is the use of matched are, more typically, partially matched cord blood cell transplants. The use of cord blood stem cells (CBSCs) is problematic, with a risk of graft failure and prolonged time to engraftment requiring extended transfusion support. Indeed, all forms of allogeneic HCT involve a 10-15% risk of transplant related mortality, and up to a 30% risk of chronic graft versus host disease.

Thus, there is a need in the art for safer and more efficient adrenoleukodystrophy therapies. The present invention provides solutions to these and other problems.

BRIEF SUMMARY

Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In various embodiments, the present invention contemplates, in part, a vector comprising: a left (5') retroviral LTR; a central polypurine tract/DNA flap (cPPT/FLAP); a retroviral export element; a promoter active in a microglial cell, operably linked to a polynucleotide encoding an ATP-binding cassette, sub-family D, member 1 (ABCD1) polypeptide; and a right (3') retroviral LTR; wherein the vector does not comprise a woodchuck post-transcriptional regulatory element (WPRE).

In particular embodiments, the vector is a lentivirus vector.

In related embodiments, the lentivirus is HIV.

In more particular embodiments, the lentivirus is HIV-1.

In certain embodiments, the promoter of the 5' LTR is replaced with a heterologous promoter.

In additional embodiments, the heterologous promoter is a cytomegalovirus (CMV) promoter, a Rous Sarcoma Virus (RSV) promoter, or an Simian Virus 40 (SV40) promoter.

In additional particular embodiments, the heterologous promoter is a CMV promoter.

In further embodiments, the 5' LTR or 3' LTR is a lentivirus LTR.

In other embodiments, the 5' LTR and 3' LTR are lentivirus LTRs.

In certain particular embodiments, the lentivirus is HIV-1.

In particular embodiments, the 3' LTR comprises one or more modifications.

In certain particular embodiments, the 3' LTR comprises one or more deletions.

In additional embodiments, the 3' LTR is a self-inactivating (SIN) LTR.

In some embodiments, the retroviral export element is a rev response element (RRE).

In further embodiments, the cPPT/FLAP is from HIV-1.

In certain embodiments, the promoter comprises a myeloproliferative sarcoma virus enhancer, negative control region deleted, dl587rev primer-binding site substituted (MND) promoter or transcriptionally active fragment thereof.

In particular embodiments, the polynucleotide encoding ABCD1 polypeptide is a cDNA.

In related embodiments, the cDNA comprises an optimized Kozak sequence.

In certain embodiments, the optimal Kozak sequence is (GCC)RCCATGG, wherein R is a purine (A or G).

In particular embodiments, the polynucleotide encodes a human ABCD1 polypeptide.

In various embodiments, the present invention contemplates, in part, a lentiviral vector comprising: a left (5') LTR; a cPPT/FLAP; an RRE; a MND promoter operably linked to a polynucleotide encoding a human ABCD1 polypeptide; a right (3') LTR; and a polyadenylation sequence; wherein the vector does not comprise a woodchuck post-transcriptional regulatory element (WPRE).

In particular embodiments, the lentiviral vector comprises a Psi (T) packaging signal.

In certain embodiments, the polyadenylation sequence is a bovine growth hormone polyadenylation or signal rabbit β-globin polyadenylation sequence.

In certain particular embodiments, the lentiviral vector comprises a 5' LTR or 3' LTR from HIV-1.

In additional embodiments, the 3' LTR is a SIN LTR.

In various embodiments, the present invention contemplates, in part, a lentiviral vector comprising: a left (5') HIV-1 LTR; a Psi (T) packaging signal; a cPPT/FLAP; an RRE; a MND promoter, operably linked to a cDNA encoding a human ABCD1 polypeptide; a right (3') self-inactivating (SIN) HIV-1 LTR; and a rabbit β-globin polyadenylation sequence; wherein the vector does not comprise a woodchuck post-transcriptional regulatory element (WPRE).

In various embodiments, the present invention contemplates, in part, a mammalian cell comprising a vector according to any one of preceding vectors described herein.

In particular embodiments, the present invention contemplates, in part, a packaging cell comprising: a first polynucleotide encoding gag, a second polynucleotide encoding pol, a third polynucleotide encoding env, and a vector according to any one of preceding vectors described herein.

In certain embodiments, the present invention contemplates, in part, a producer cell comprising a vector according to any one of preceding vectors described herein.

In additional embodiments, the present invention contemplates, in part, vector particles produced by the producer cell.

In various particular embodiments, the present invention contemplates, in part, a vector comprising: at least one LTR; a central polypurine tract/DNA flap (cPPT/FLAP); a retroviral export element; and a promoter active in a microglial cell, operably linked to a polynucleotide encoding an ATP-binding cassette, sub-family D, member 1 (ABCD1) polypeptide; wherein the vector does not comprise a woodchuck post-transcriptional regulatory element (WPRE).

In various certain embodiments, the present invention contemplates, in part, a vector comprising: at least one LTR; a cPPT/FLAP; an RRE; a MND promoter operably linked to a polynucleotide encoding a human ABCD1 polypeptide; and a polyadenylation sequence; wherein the vector does not comprise a woodchuck post-transcriptional regulatory element (WPRE).

In various additional embodiments, the present invention contemplates, in part, a vector comprising: at least one SIN HIV-1 LTR; a Psi (Ψ) packaging signal; a cPPT/FLAP; an RRE; a MND promoter, operably linked to a cDNA encoding a human ABCD1 polypeptide; and a rabbit β-globin polyadenylation sequence, wherein the vector does not comprise a woodchuck post-transcriptional regulatory element (WPRE).

In various embodiments, the present invention contemplates, in part, a host cell transduced with the vector. In particular embodiments, the host cell is an embryonic stem cell, a somatic stem cell, or a progenitor cell.

In certain embodiments, the cell is a hematopoietic stem cell.

In particular embodiments, the present invention further contemplates, in part use of the viral vectors of the invention in gene therapy.

In preferred embodiments, the gene therapy treats or prevents adrenoleukodystrophy or adrenomyeloneuropathy.

In various other embodiments, the present invention contemplates, in part, a method of treating adrenoleukodystrophy or adrenomyeloneuropathy, comprising administering to a subject a cell transduced with a vector of the invention.

In particular embodiments, the cell is an embryonic stem cell, a somatic stem cell, or a progenitor cell.

In certain embodiments, the cell is a hematopoietic stem cell.

BRIEF DESCRIPTION OF THE SEQUENCE IDENTIFIERS

SEQ ID NO: 1 is a cDNA sequence that encodes human ABCD1.

SEQ ID NO: 2 is a cDNA sequence that encodes human ABCD1.

SEQ ID NO: 3 is a MND promoter polynucleotide sequence.

Figure 2:
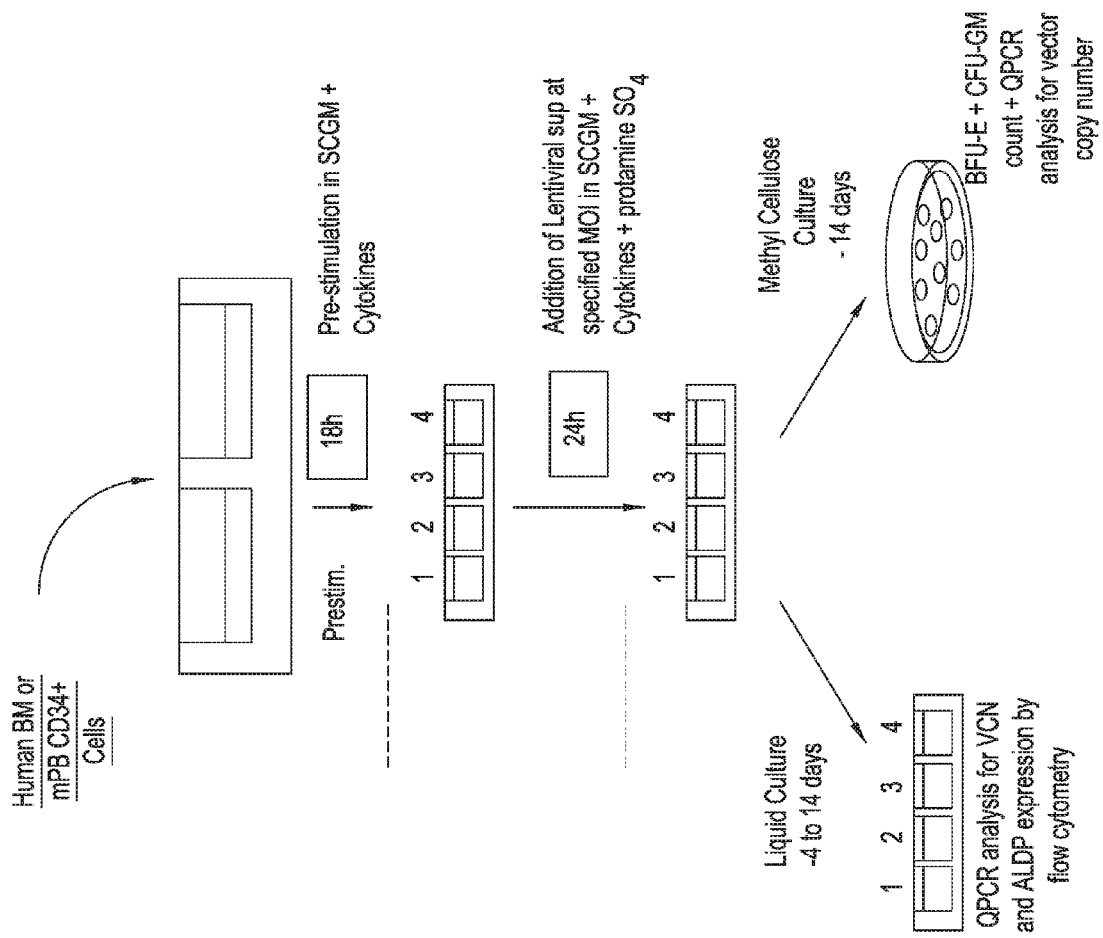

FIG. 2 shows transduction with pLBP100 and pLBP140 lentiviral vectors and short-term liquid and methycellulose cultures in experiments.

Figure 3:
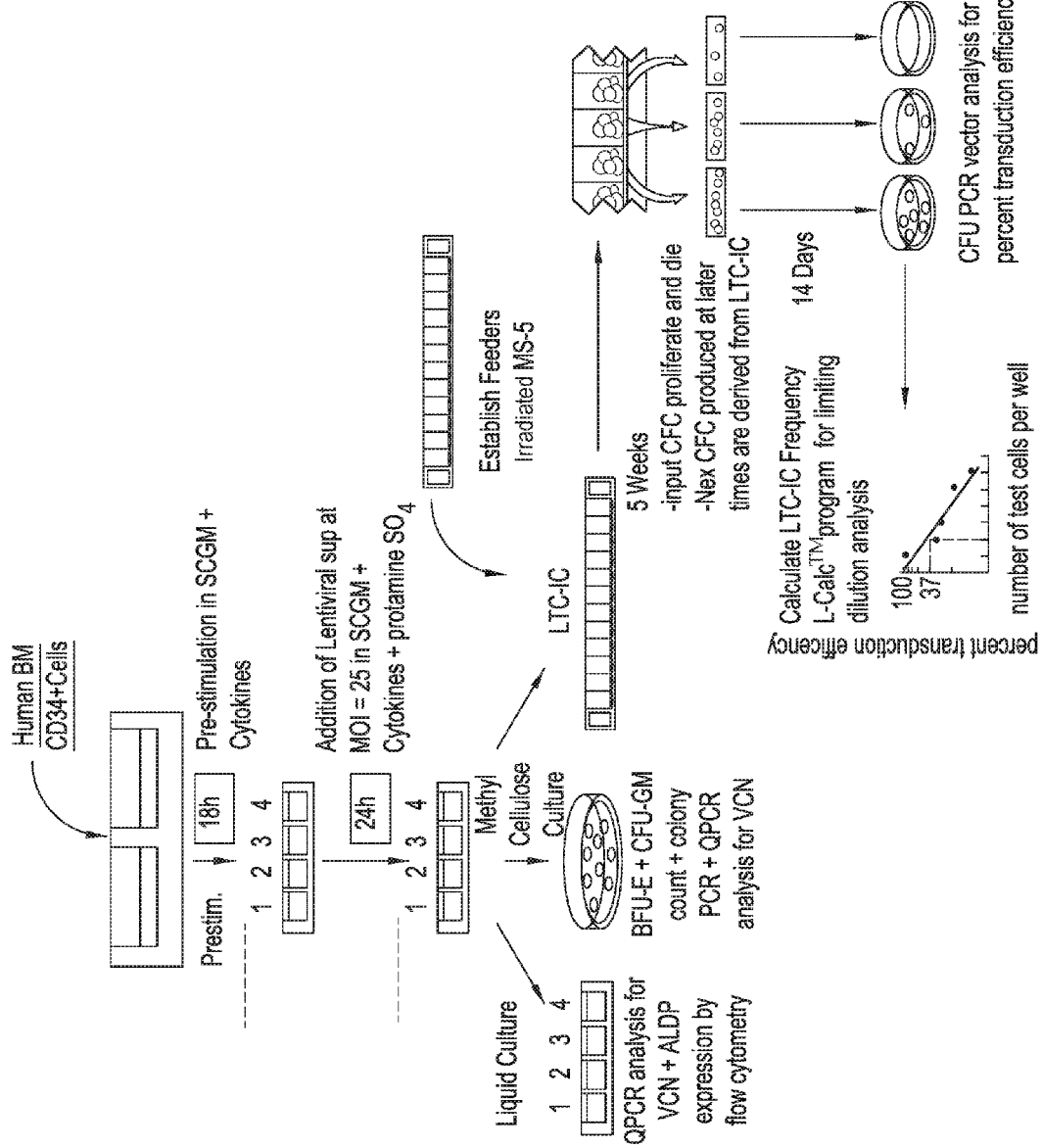

FIG. 3 shows transduction with pLBP100 and pLBP140 lentiviral vectors followed by short-term liquid and methycellulose cultures or long-term culture on supporting MS5 stromas.

Figure 4A:
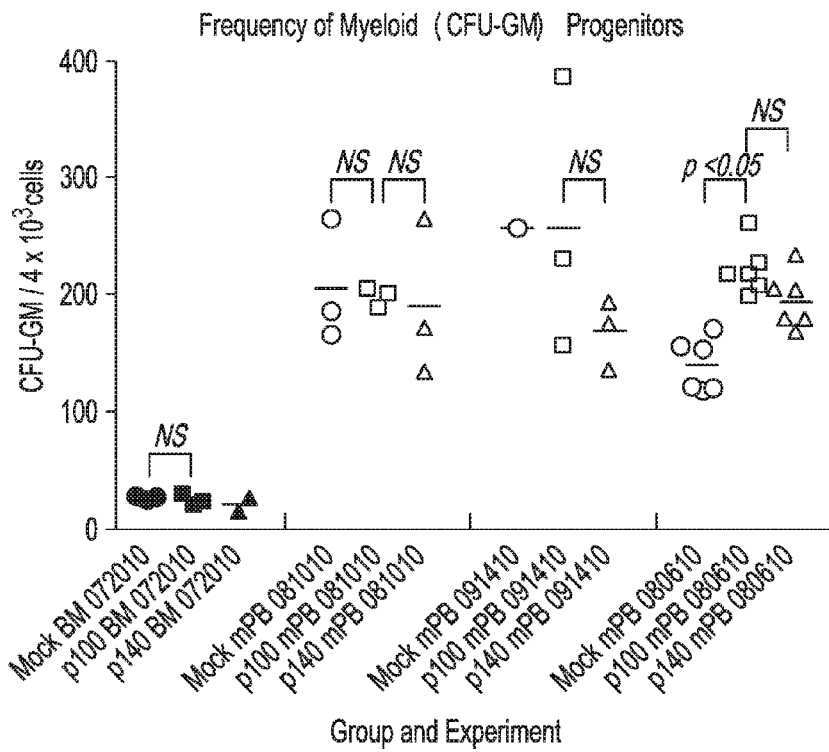
Figure 4B:
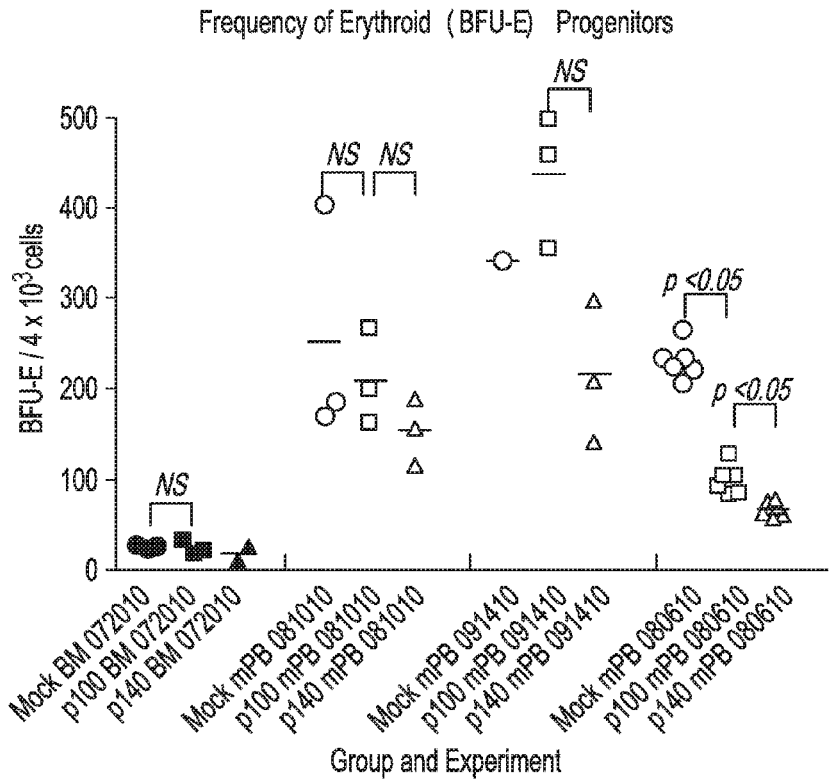

FIG. 4 shows the number of myeloid (CFU-GM; FIG. 4A) and erythroid (BFU-E; FIG. 4B) progenitors after transduction of normal human CD34+ cells. Transductions were performed using either pLBP100 (p100) or pLBP140 (p140) involving four separate experiments.

Figure 5:
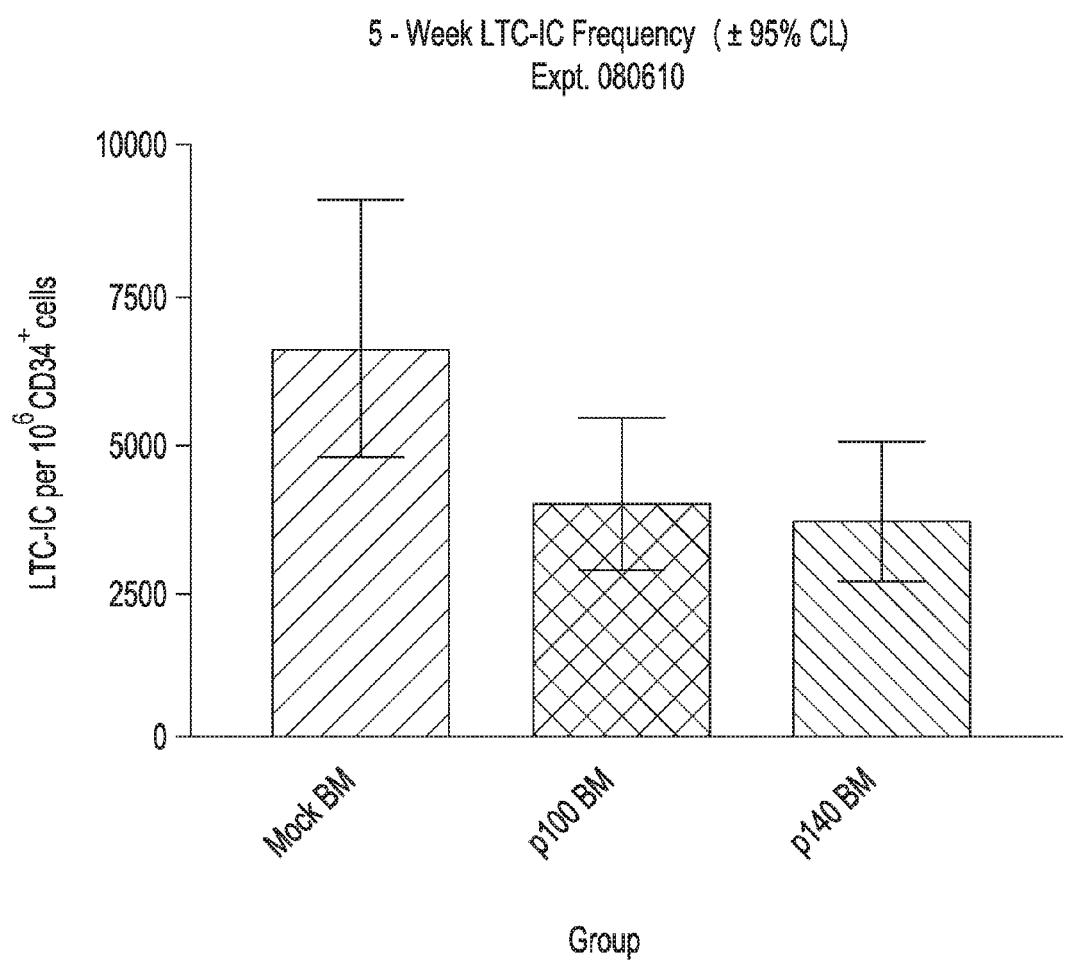

FIG. 5 shows the frequency of LTC-ICs. Following limiting dilution and 5-week stromal co-culture with transfer into methylcellulose cultures for enumeration of secondary CFCs and estimation of frequencies with 95% confidence intervals using the L-Calc™ program.

Figure 6A:
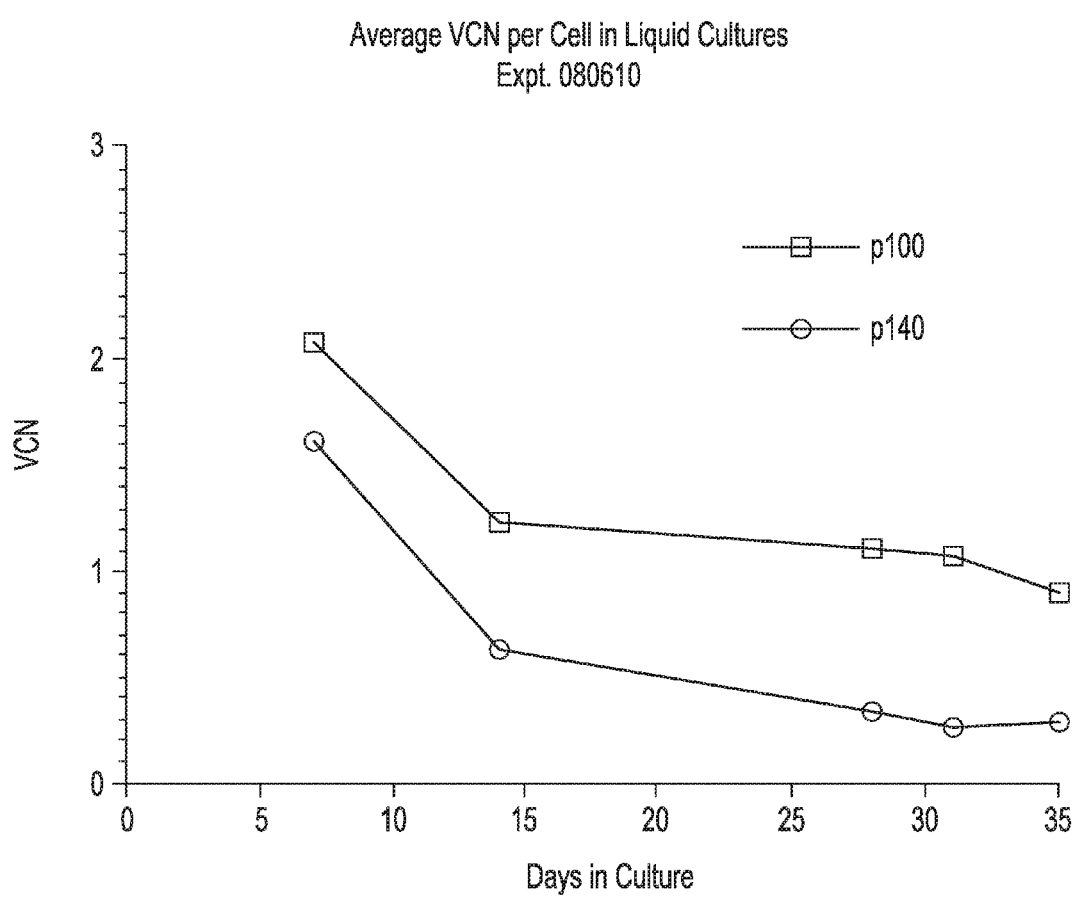
Figure 6B:
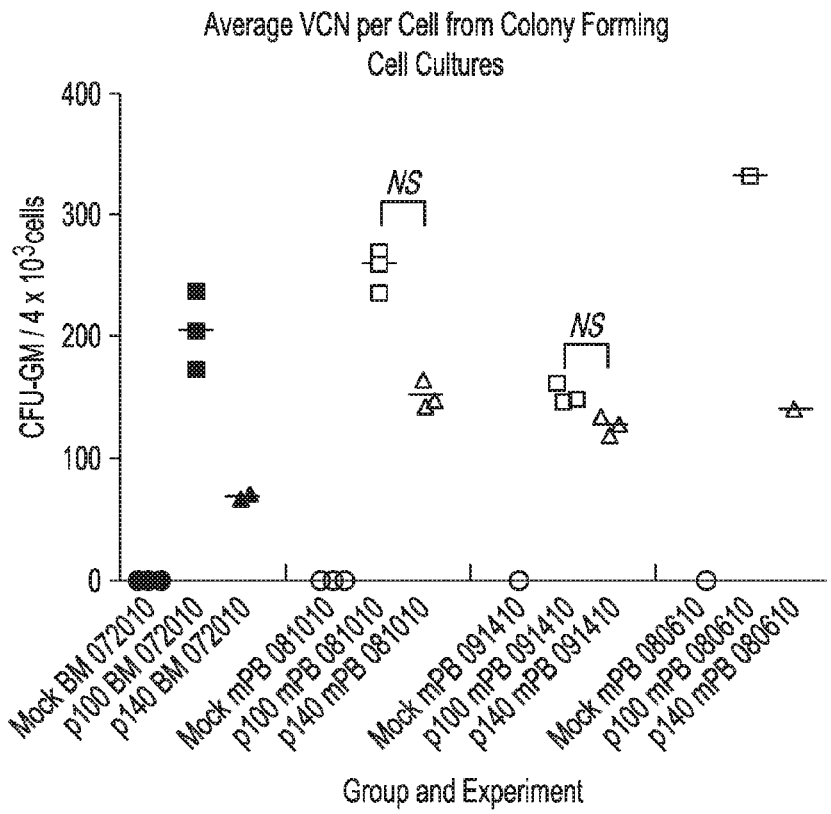
Figure 6C:
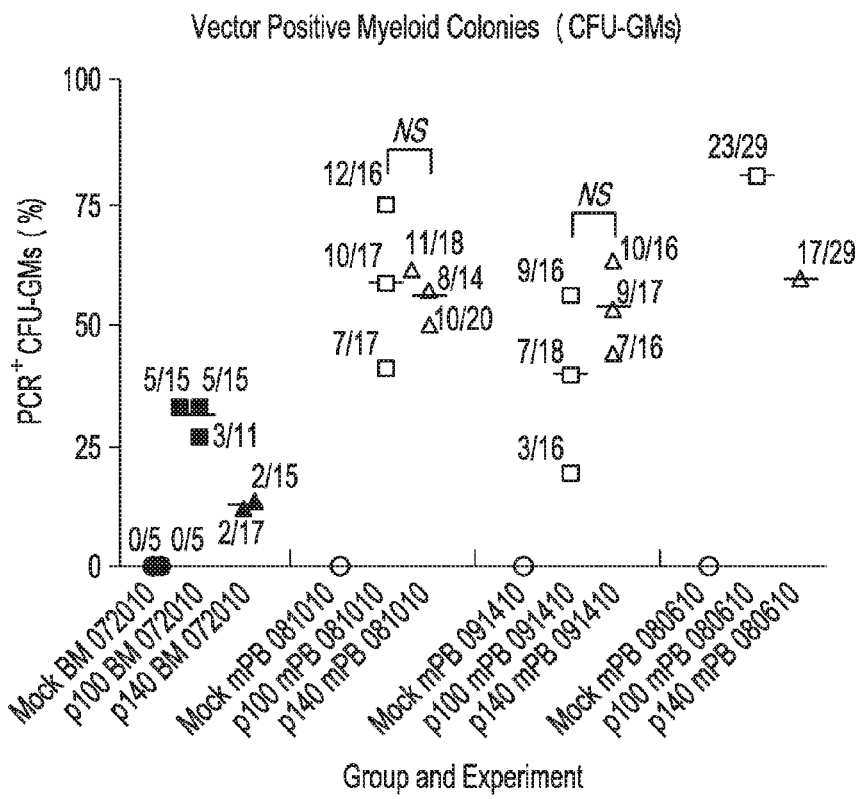

FIG. 6 shows the efficiency of vector integration in short-term progenitors. (A) Vector copy number (VCN) on cells at 7, 14, 28, 31 and 35 days in liquid culture. (B) Average VCN from pooled day 14 CFC cultures. (C) Percent vector positive myeloid colonies. The positive and total colony numbers analyzed are indicated.

Figure 7A:
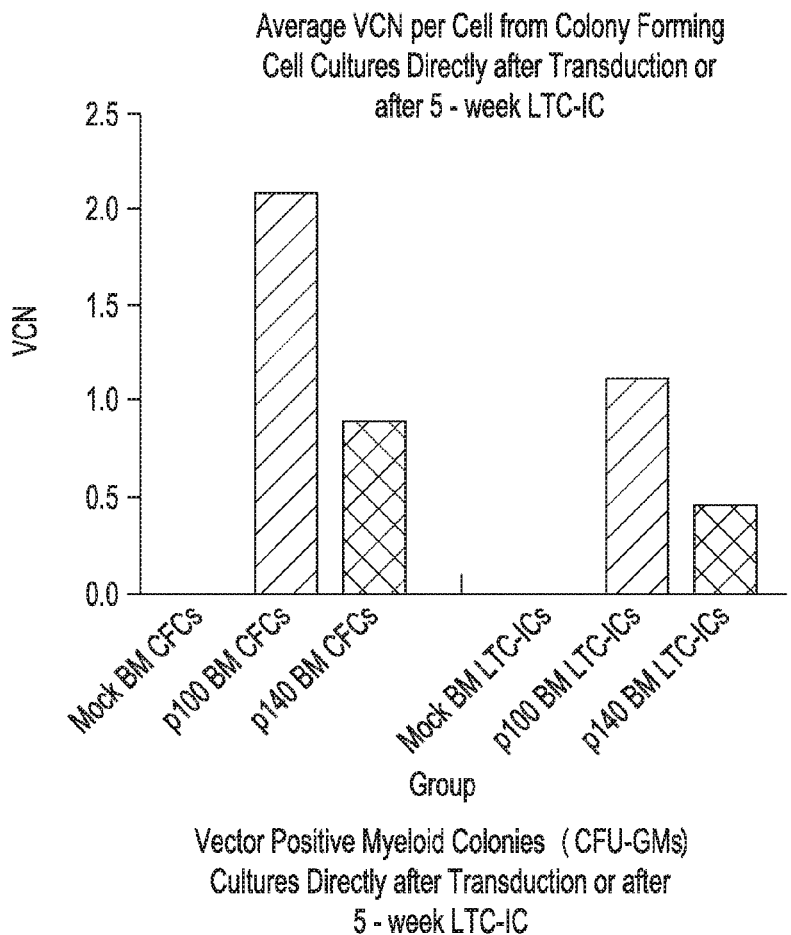
Figure 7B:
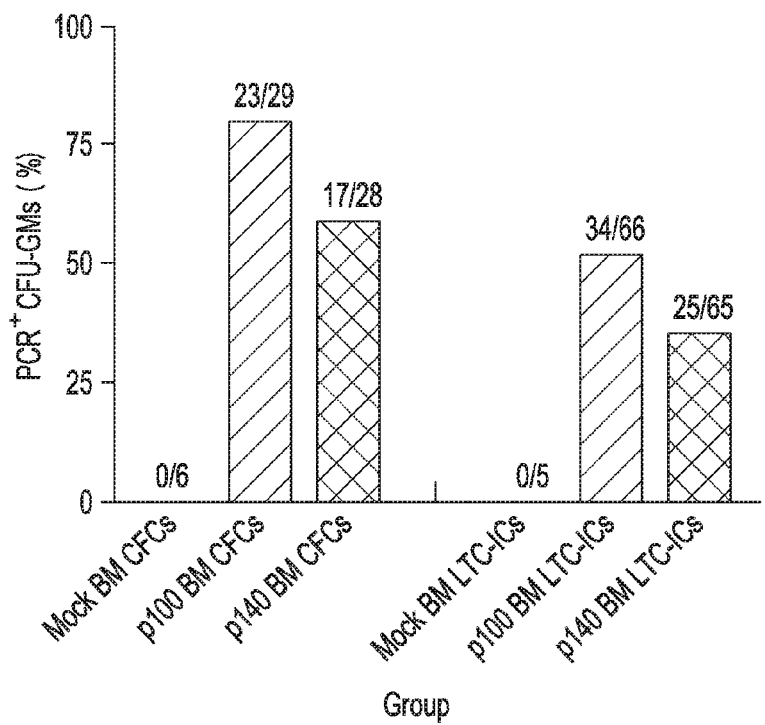

FIG. 7 shows the efficiency of vector integration in short-term versus long-term (LTC-IC) progenitors. (A) Average VCN from pooled day 14 CFC cultures. (B) Percent vector positive myeloid colonies. The positive and total colony numbers analyzed are indicated.

Figure 8B:
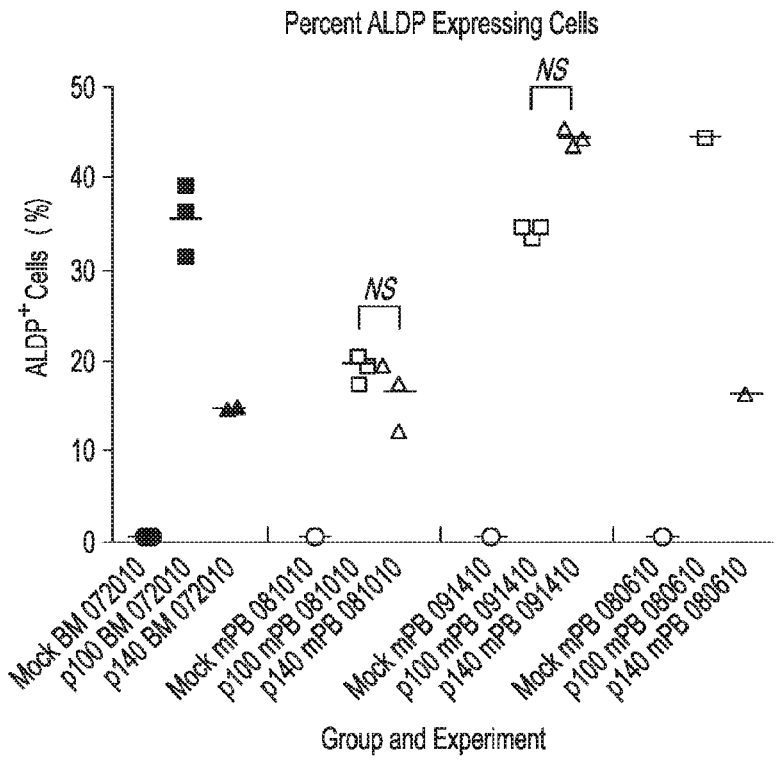
Figure 8C:
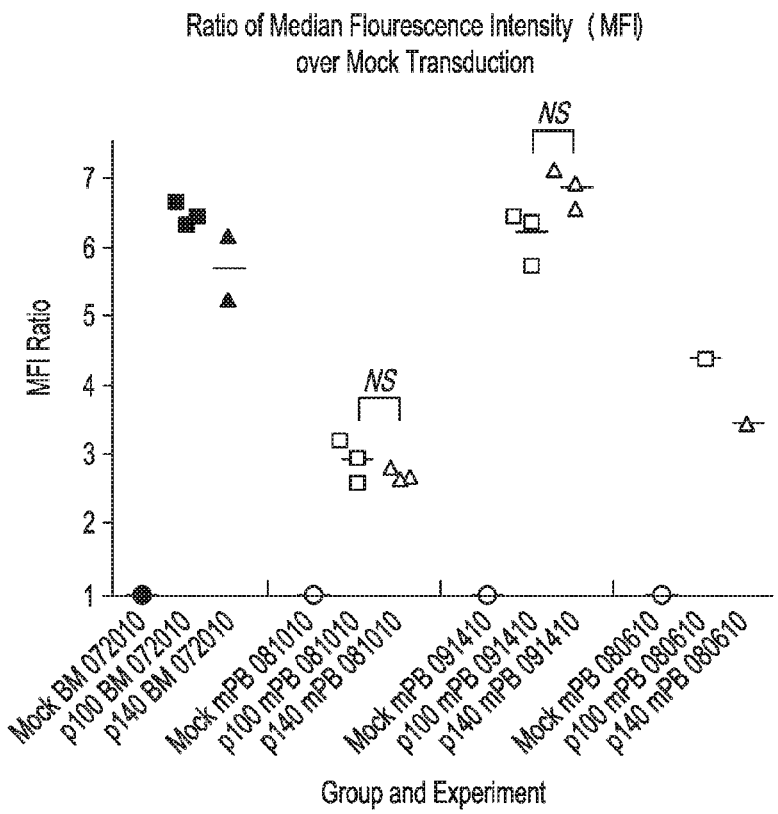

FIG. 8 shows ALD protein (ALDP) expression in transduced cells by flow cytometry. (A1 and A2) Histograms showing PE fluorescence for mock, pLBP100 and pLBP140 transduced cells from different experiments. (B) Percent ALDP positive cells at 7 days (expts. 072010 and 091410), 14 days (expt. 081010) and 28 days (expt. 080610). (C) MFI as a ratio over mock controls showing relative levels of ALDP expression among ALDP+ cells.

Figure 9:
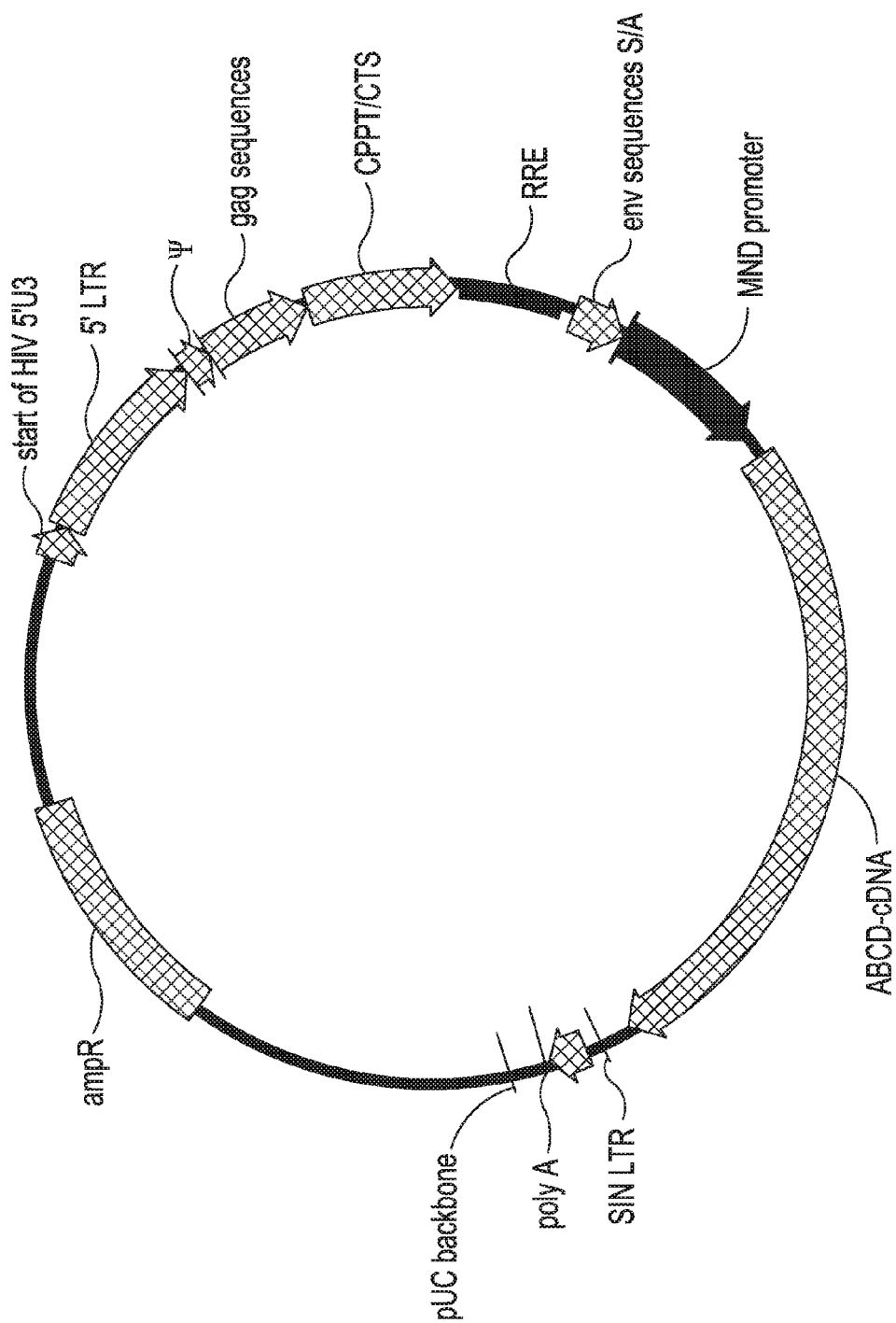

FIG. 9 shows a schematic map of an MND-ALD vector construct. The vector has the human ABCD-1 cDNA under the control of the MND promoter for high-level expression. HIV LTR, human immunodeficiency type-1 virus long terminal repeat; Ψ+, packaging signal; cPPT/flap, central polypurine tract; RRE, Rev-responsive element; ppt, polypurine tract. The vector does not contain a WPRE sequence.

Figure 10:
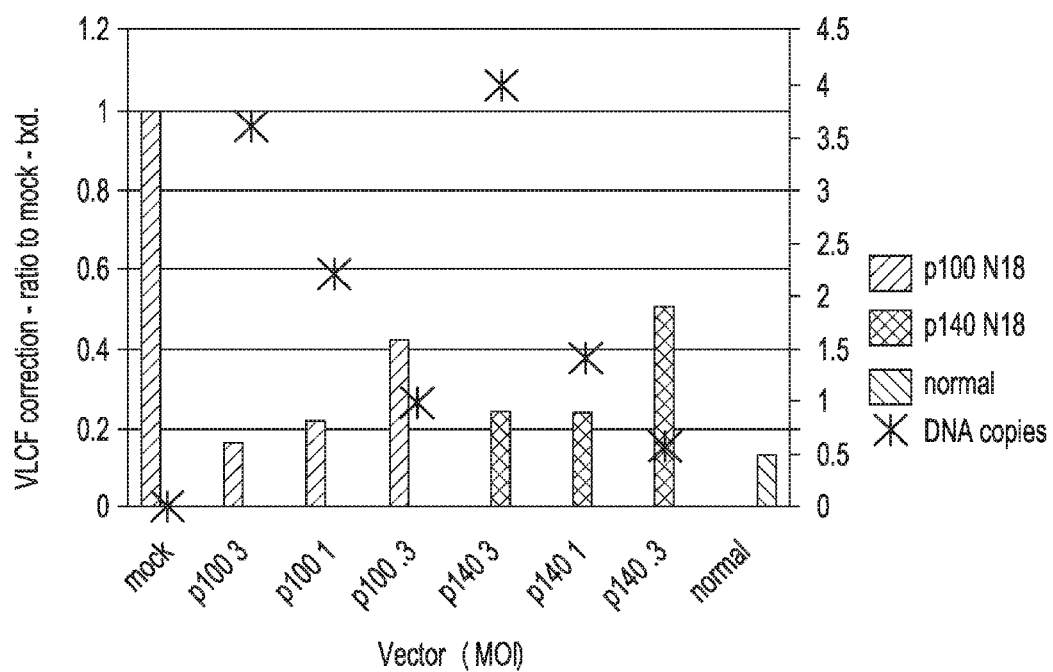

FIG. 10 shows the ratio of VLCFA correction to mock versus VCN in 4496 cells transduced with p100 and p140 at various MOI.

DETAILED DESCRIPTION

A. Overview

The present invention is generally directed to safer and more efficient viral vectors and transduced cell therapies for adrenoleukodystrophies and adrenomyeloneuropathies. Without wishing to be bound by any particular theory, Applicants contemplate that the hematopoietic stems cells of boys with ALD are otherwise normal and because microglia are of bone marrow origin, the supplementation of defective ABCD1 gene with the normal ABCD1 cDNA in the subjects' hematopoietic stem cells could lead to normalization of ALDP levels in the brain microglia. Thus, ex vivo gene transfer of the normal ABCD1 cDNA into autologous CD34+ hematopoietic stems cells using vectors of the present invention, followed by transplantation after bone marrow ablation, can result in the stabilization of CNS function and a drop in plasma VLCFA levels associated with the lethal effects of ALD.

Accordingly, the compositions and methods of the present invention could represent a significant medical advance in the treatment of boys with ALD, since it will allow for rapid treatment with a significantly decreased risk of hematopoietic engraftment failure and elimination of acute and chronic GvHD. Time is very much of the essence in this population because of the potential for rapid CNS deterioration and the 12-18 month wait before disease stabilization seen with HCT.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. 1 & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); *A Practical Guide to Molecular Cloning* (B. Perbal, ed., 1984).

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. For the purposes of the present invention, the following terms are defined below.

As used herein, the term "retrovirus" refers an RNA virus that reverse transcribes its genomic RNA into a linear double-stranded DNA copy and subsequently covalently integrates its genomic DNA into a host genome. Retroviruses belong to the family Retroviridae, which is composed of numerous non-icosahedral, enveloped viruses which possess two copies of a single-stranded RNA genome that has a short dimerized region. Retroviruses are a common tool for gene delivery (Miller, 2000, *Nature*. 357: 455-460). Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative retroviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

Retroviral vectors and more particularly lentiviral vectors may be used in practicing the present invention. Accordingly, the term "retrovirus" or "retroviral vector", as used herein is meant to include "lentivirus" and "lentiviral vectors" respectively.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), cosmids, bacterial artificial chromosomes, and viral vectors. Useful viral vectors include, e.g., replication defective retroviruses and lentiviruses.

As will be evident to one of skill in the art, the term "viral vector" is widely used refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements that are primarily derived from a retrovirus. The term "lentiviral vector" refers to a viral vector or plasmid containing structural and functional genetic elements, including LTRs that are primarily derived from a lentivirus. The term "hybrid" refers to a vector, LTR or other nucleic acid containing both retroviral, e.g., lentiviral, sequences and non-lentiviral viral sequences. In one embodiment, a hybrid vector refers to a vector or transfer plasmid comprising retroviral e.g., lentiviral, sequences for reverse transcription, replication, integration and/or packaging and alphavirus subgenomic promoter sequences, non-structural proteins, and/or polymerase recognition sites.

In particular embodiments, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the invention and are present in DNA form in the DNA plasmids of the invention.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R and U5 regions, appears at both the both the 5' and 3' ends of the viral genome. Adjacent to the 5' LTR are sequences necessary for reverse transcription of the genome (the tRNA primer binding site) and for efficient packaging of viral RNA into particles (the Psi site).

As used herein, the term "packaging signal" or "packaging sequence" refers to sequences located within the retroviral genome which are required for insertion of the viral RNA into the viral capsid or particle, see e.g., Clever et al., 1995 J. of Virology, Vol. 69, No. 4; pp. 2101-2109. Several retroviral vectors use the minimal packaging signal (also referred to as the psi [Ψ] sequence) needed for encapsidation of the viral genome. Thus, as used herein, the terms "packaging sequence," "packaging signal," "psi" and the symbol "Ψ," are used in reference to the non-coding sequence required for encapsidation of retroviral RNA strands during viral particle formation.

In various embodiments, vectors comprise modified 5' LTR and/or 3' LTRs. Modifications of the 3' LTR are often made to improve the safety of lentiviral or retroviral systems by rendering viruses replication-defective. As used herein, the term "replication-defective" refers to virus that is not capable of complete, effective replication such that infective virions are not produced (e.g., replication-defective lentiviral progeny). The term "replication-competent" refers to wild-type virus or mutant virus that is capable of replication, such that viral replication of the virus is capable of producing infective virions (e.g., replication-competent lentiviral progeny).

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In a further embodiment of the invention, the 3' LTR is modified such that the U5 region is replaced, for example, with an ideal poly(A) sequence. It should be noted that modifications to the LTRs such as modifications to the 3' LTR, the 5' LTR, or both 3' and 5' LTRs, are also included in the invention.

An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system.

In some embodiments, viral vectors comprise a TAR element. The term "TAR" refers to the "trans-activation response" genetic element located in the R region of lentiviral (e.g., HIV) LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, Cell, 101:173. During HIV-1 reverse transcription, central initiation of the plus-strand DNA at the central polypurine tract (cPPT) and central termination at the central termination sequence (CTS) lead to the formation of a three-stranded DNA structure: the HIV-1 central DNA flap. While not wishing to be bound by any theory, the DNA flap may act as a cis-active determinant of lentiviral genome nuclear import and/or may increase the titer of the virus. In particular embodiments, the retroviral or lentiviral vector backbones comprise one or more FLAP elements upstream or downstream of the heterologous genes of interest in the vectors. For example, in particular embodiments a transfer plasmid includes a FLAP element. In one embodiment, a vector of the invention comprises a FLAP element isolated from HIV-1.

In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol.* 65: 1053; and Cullen et al., 1991. *Cell* 58: 423), and the hepatitis B virus post-transcriptional regulatory element (HPRE). Generally, the RNA export element is placed within the 3' UTR of a gene, and can be inserted as one or multiple copies.

In particular embodiments, expression of heterologous sequences in viral vectors is increased by incorporating posttranscriptional regulatory elements, and efficient polyadenylation sites and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, *J. Virol.*, 73:2886); the posttranscriptional regulatory element present in hepatitis B virus (HPRE) (Huang et al., *Mol. Cell. Biol.*, 5:3864); and the like (Liu et al., 1995, *Genes Dev.*, 9:1766). The posttranscriptional regulatory element is generally positioned at the 3' end the heterologous nucleic acid sequence. This configuration results in synthesis of an mRNA transcript whose 5' portion comprises the heterologous nucleic acid coding sequences and whose 3' portion comprises the posttranscriptional regulatory element sequence. In preferred embodiments, vectors of the invention lack or do not comprise a posttranscriptional regulatory element such as a WPRE or HPRE because in some instances these elements increase the risk of cellular transformation and/or do not substantially or significantly increase the amount of mRNA transcript or increase mRNA stability. Therefore, in some embodiments, vectors of the invention lack or do not comprise a WPRE or HPRE as an added safety measure.

Elements directing the efficient termination and polyadenylation of the heterologous nucleic acid transcripts increases heterologous gene expression. Transcription termination signals are generally found downstream of the polyadenylation signal. The term "polyA site" or "polyA sequence" as used herein denotes a DNA sequence which directs both the termination and polyadenylation of the nascent RNA transcript by RNA polymerase II. Efficient polyadenylation of the recombinant transcript is desirable as transcripts lacking a poly A tail are unstable and are rapidly degraded. Illustrative examples of polyA signals that can be used in a vector of the invention, includes an ideal polyA sequence (e.g., AATAAA, ATTAAA AGTAAA), a bovine growth hormone polyA sequence (BGHpA), a rabbit β-globin polyA sequence (rβgpA), or another suitable heterologous or endogenous polyA sequence known in the art.

In certain embodiments, a retroviral or lentiviral vector further comprises an insulator element. Insulators elements may contribute to protecting lentivirus-expressed sequences, e.g., therapeutic polypeptides, from integration site effects, which may be mediated by cis-acting elements present in genomic DNA and lead to deregulated expression of transferred sequences (i.e., position effect; see, e.g., Burgess-Beusse et al., 2002, *Proc. Natl. Acad. Sci.*, USA, 99:16433; and Zhan et al., 2001, *Hum. Genet.*, 109:471). In some embodiments, transfer vectors comprise an insulator element in one or both LTRs or elsewhere in the region of the vector that integrates into the cellular genome. Suitable insulators for use in the invention include, but are not limited to, the chicken β-globin insulator (see Chung et al., 1993. *Cell* 74:505; Chung et al., 1997. *PNAS* 94:575; and Bell et al., 1999. *Cell* 98:387, incorporated by reference herein). Examples of insulator elements include, but are not limited to, an insulator from an β-globin locus, such as chicken HS4.

According to certain specific embodiments of the invention, most or all of the viral vector backbone sequences are derived from a lentivirus, e.g., HIV-1. However, it is to be understood that many different sources of lentiviral sequences can be used, and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, any of which may be adapted to produce a viral vector or transfer plasmid of the present invention.

As used herein, the terms "polynucleotide" or "nucleic acid" refers to messenger RNA (mRNA), RNA, genomic RNA (gRNA), plus strand RNA (RNA(+)), minus strand RNA (RNA(−)), genomic DNA (gDNA), complementary DNA (cDNA) or DNA. Polynucleotides include single and double stranded polynucleotides. Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. In various illustrative embodiments, the present invention contemplates, in part, viral vector and transfer plasmid polynucleotide sequences and compositions comprising the same. In particular embodiments, the invention provides polynucleotides encoding therapeutic polypeptides.

As used herein; the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

As used herein, the term "isolated" means material that is substantially or essentially free from components that normally accompany it in its native state. For example, an "isolated polynucleotide," as used herein, refers to a polynucleotide that has been purified from the sequences which flank it in a naturally-occurring state, e.g., a DNA fragment that has been removed from the sequences that are normally adjacent to the fragment.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The term 'nucleic acid cassette" as used herein refers to genetic sequences within the vector which can express a RNA, and subsequently a protein. The nucleic acid cassette contains the gene of interest. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment of the invention, the nucleic acid cassette contains the sequence of a therapeutic gene used to treat adrenoleukodystrophy or adrenomyeloneuropathy. The cassette can be removed and inserted into a plasmid or viral vector as a single unit.

Polynucleotides include a polynucleotide-of-interest. As used herein, the term "polynucleotide-of-interest" refers to the polynucleotide, e.g., a polynucleotide encoding a polypeptide (i.e., a polypeptide-of-interest), inserted into an expression vector that is desired to be expressed. In certain embodiments, the polynucleotide-of-interest encodes a polypeptide that provides a therapeutic effect in the treatment or prevention of a disease or disorder, which may be referred to as a "therapeutic polypeptide," e.g., ATP-binding cassette, sub-family D (ALD), member 1 (ABCD1) gene. Polynucleotides-of-interest, and polypeptides encoded therefrom, include both polynucleotides that encode wild-type polypeptides, as well as functional variants and fragments thereof. In particular embodiments, a functional variant has at least 80%, at least 90%, at least 95%, or at least 99% identity to a corresponding wild-type reference polynucleotide or polypeptide sequence. In certain embodiments, a functional variant or fragment has at least 50%, at least 60%, at least 70%, at least 80%, or at least 90% of a biological activity of a corresponding wild-type polypeptide. Representative polynucleotides sequences suitable for use in the present invention include, but are not limited to, the human ACBD1 cDNAs set forth in SEQ ID NOs: 1-2.

The polynucleotides of the present invention, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

The term "promoter" as used herein refers to a recognition site of a polynucleotide (DNA or RNA) to which an RNA polymerase binds. The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions. In one embodiment, a vector of the invention comprises a myeloproliferative sarcoma virus enhancer, negative control region deleted, dl587rev primer-binding site substituted (MND) promoter (Challita et al., *J Virol.* 69(2):748-55 (1995); SEQ ID NO: 3).

In particular embodiments, a vector of the invention comprise exogenous, endogenous, or heterologous control sequences such as promoters and/or enhancers. An "endogenous" control sequence is one which is naturally linked with a given gene in the genome. An "exogenous" control sequence is one which is placed in juxtaposition to a gene by means of genetic manipulation (i.e., molecular biological techniques) such that transcription of that gene is directed by the linked enhancer/promoter. A "heterologous" control sequence is an exogenous sequence that is from a different species than the cell being genetically manipulated.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive promoter" refers to a promoter that continually or continuously allows for transcription of an operably linked sequence. Constitutive promoters may be a "ubiquitous promoter" that allows expression in a wide variety of cell and tissue types or a "tissue-specific promoter" that allows expression in a restricted variety of cell and tissue types. Illustrative ubiquitous promoters include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, and a β-actin promoter.

In a particular embodiment, it may be desirable to use a tissue-specific promoter to achieve cell type specific, lineage specific, or tissue-specific expression of a desired polynucleotide sequence (e.g., to express a particular nucleic acid encoding a polypeptide in only a subset of cell types or tissues or during specific stages of development). Illustrative examples of tissue specific promoters include, but are not limited to: an B29 promoter (B cell expression), a runt transcription factor (CBFa2) promoter (stem cell specific expression), an CD14 promoter (monocytic cell expression), an CD43 promoter (leukocyte and platelet expression), an CD45 promoter (hematopoietic cell expression), an CD68 promoter (macrophage expression), a CYP450 3A4 promoter (hepatocyte expression), an desmin promoter (muscle expression), an elastase 1 promoter (pancreatic acinar cell expression, an endoglin promoter (endothelial cell expression), a fibroblast specific protein 1 promoter (FSP1) promoter (fibroblast cell expression), a fibronectin promoter (fibroblast cell expression), a fms-related tyrosine kinase 1 (FLT1) promoter (endothelial cell expression), a glial fibrillary acidic protein (GFAP) promoter (astrocyte expression), an insulin promoter (pancreatic beta cell expression), an integrin, alpha 2b (ITGA2B) promoter (megakaryocytes), an intracellular adhesion molecule 2 (ICAM-2) promoter (endothelial cells), an interferon beta (IFN-β) promoter (hematopoietic cells), a keratin 5 promoter (keratinocyte expression), a myoglobin (MB) promoter (muscle expression), a myogenic differentiation 1 (MYOD1) promoter (muscle expression), a nephrin promoter (podocyte expression), a bone gamma-carboxyglutamate protein 2 (OG-2) promoter (osteoblast expression), an 3-oxoacid CoA transferase 2B (Oxct2B) promoter, (haploid-spermatid expression), a surfactant protein B (SP-B) promoter (lung expression), a synapsin promoter (neuron expression), a Wiskott-Aldrich syndrome protein (WASP) promoter (hematopoietic cell expression).

In one embodiment, a vector of the present invention comprises a tissue specific promoter and/or enhancer that expresses a desired polypeptide, e.g., ABCD1, in microglial cells, e.g., an MND promoter (SEQ ID NO: 3).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue-specific expression. Certain embodiments of the invention provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene*, 323:67), the cumate inducible gene switch (WO 2002/088346), tetracycline-dependent regulatory systems, etc.

Conditional expression can also be achieved by using a site-specific DNA recombinase. According to certain embodiments of the invention the vector comprises at least one (typically two) site(s) for recombination mediated by a site-specific recombinase. As used herein, the terms "recombinase" or "site-specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments of the present invention include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The vectors may comprise one or more recombination sites for any of a wide variety of site-specific recombinases. It is to be understood that the target site for a site-specific recombinase is in addition to any site(s) required for integration of a vector, e.g., a retroviral vector or lentiviral vector. As used herein, the terms "recombination sequence," "recombination site," or "site-specific recombination site" refer to a particular nucleic acid sequence to which a recombinase recognizes and binds.

Figure 1:
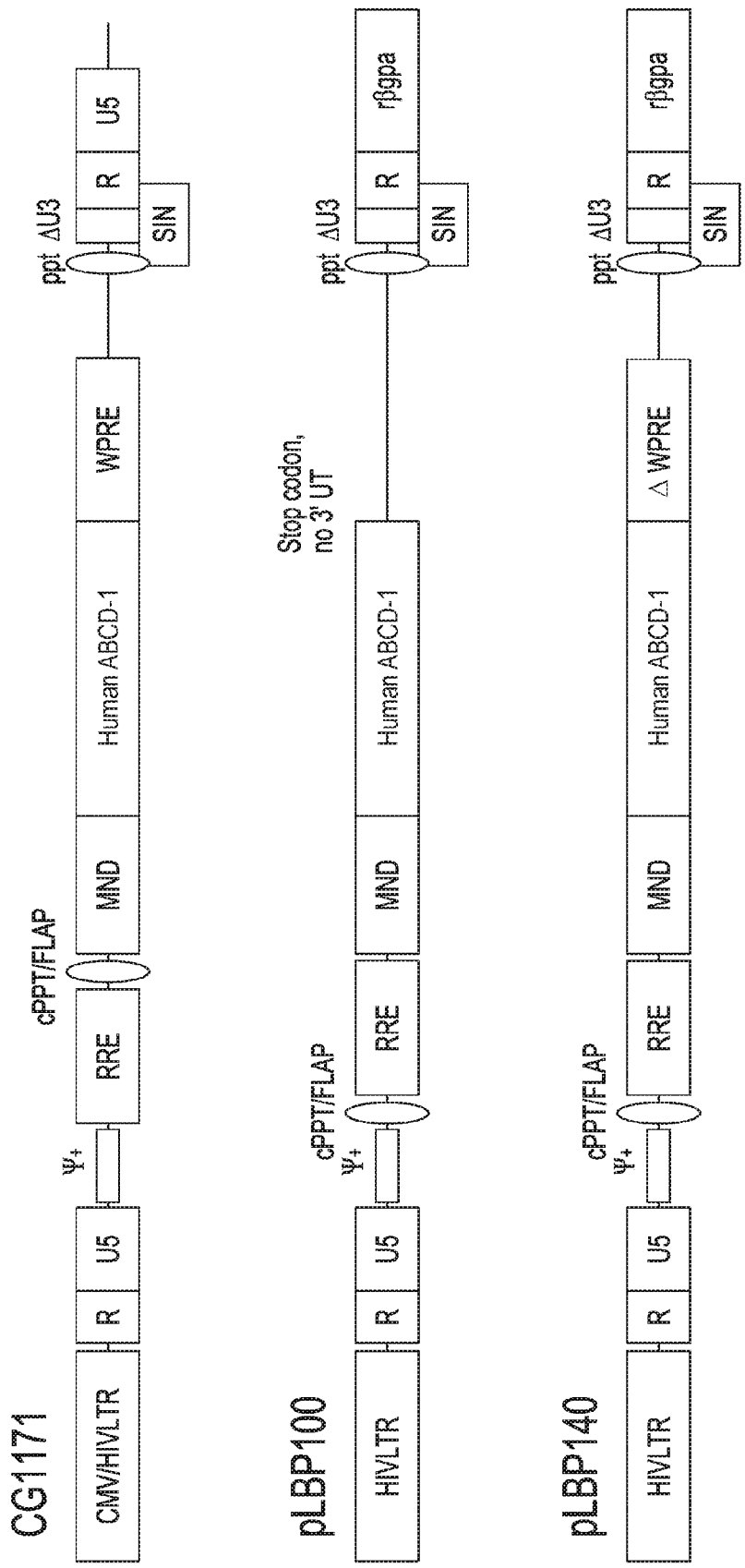
FIG. 1 shows a schematic map of MND-ALD vector constructs used in preclinical and clinical studies. All vectors have the human ABCD-1 cDNA under the control of the MND promoter for high-level expression. Safety modifications to pLBP100 and pLBP140 include: 2 stop codons in the gag coding region, a 400 bp deletion in the U3 of the right HIV LTR and the rabbit β-globin polyA (rβgppA) signal. HIV LTR, human immunodeficiency type-1 virus long terminal repeat; Ψ+, packaging signal; cPPT/flap, central polypurine tract; RRE, Rev-responsive element; ppt, polypurine tract. The pLBP140 differs from the pLBP100 vector by introduction of the mutated (mut6) but functional, woodchuck hepatitis virus post-transcriptional regulatory element (ΔWPRE).

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., *Current Opinion in Biotechnology* 5:521-527 (1994)). Other exemplary loxP sites include, but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), $F_1$, $F_2$, $F_3$ (Schlake and Bode, 1994), $F_4$, $F_5$ (Schlake and Bode, 1994), FRT(LE) (Senecoff et al., 1988), FRT(RE) (Senecoff et al., 1988).

Other examples of recognition sequences are the attB, attP, attL, and attR sequences, which are recognized by the recombinase enzyme λ Integrase, e.g, phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagarajan et al., 2001; Belteki et al., 2003). Thus, typical strategies position by homologous recombination an attP-bearing "docking site" into a defined locus, which is then partnered with an attB-bearing incoming sequence for insertion.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. In particular embodiments, the vectors contemplated by the invention, include one or more polynucleotides-of-interest that encode one or more polypeptides. To achieve efficient translation of each of the plurality of polypeptides, the polynucleotide sequences can be separated by one or more IRES sequences or polynucleotide sequences encoding self-cleaving polypeptides.

As used herein, the term "Kozak sequence" refers to a short nucleotide sequence that greatly facilitates the initial binding of mRNA to the small subunit of the ribosome and increases translation. The consensus Kozak sequence is (GCC)RCCATGG, where R is a purine (A or G) (Kozak, 1986. *Cell.* 44(2):283-92, and Kozak, 1987. *Nucleic Acids Res.* 15(20):8125-48). In particular embodiments, the vectors contemplated by the invention, comprise polynucleotides that have a consensus Kozak sequence and that encode a desired polypeptide, e.g., ABCD1.

In particular embodiments, vectors comprise a polyadenylation sequence 3' of a polynucleotide encoding a polypeptide to be expressed. Polyadenylation sequences can promote mRNA stability by addition of a polyA tail to the 3' end of the coding sequence and thus, contribute to increased translational efficiency. Recognized polyadenylation sites include an ideal polyA sequence (e.g., AATAAA, ATTAAA AGTAAA), a bovine growth hormone polyA sequence (BGHpA), a rabbit β-globin polyA sequence (rβgpA), or another suitable heterologous or endogenous polyA sequence known in the art.

In certain embodiments, vectors comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al., 1977. *Cell* 11:223-232) and adenine phosphoribosyltransferase (Lowy et al., 1990. *Cell* 22:817-823) genes which can be employed in tk- or aprt- cells, respectively.

A "host cell" includes cells transfected or infected in vivo or in vitro with a recombinant vector or a polynucleotide of the invention. Host cells may include packaging cells, producer cells, and cells infected with viral vectors. In particular embodiments, host cells infected with viral vector of the invention are administered to a subject in need of therapy.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A retroviral/lentiviral transfer vector of the present invention can be introduced into a packaging cell line, via transfection, transduction or infection, to generate a producer cell or cell line. The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neomycin, hygromycin, puromycin, blastocidin, zeocin, thymidine kinase, DHFR, Gln synthetase or ADA, followed by selection in the presence of the appropriate drug and isolation of clones. A selectable marker gene can be linked physically to genes encoding by the packaging vector, e.g., by IRES or self cleaving viral peptides.

Viral envelope proteins (env) determine the range of host cells which can ultimately be infected and transformed by recombinant retroviruses generated from the cell lines. In the case of lentiviruses, such as HIV-1, HIV-2, SIV, FIV and EIV, the env proteins include gp41 and gp120. Preferably, the viral env proteins expressed by packaging cells of the invention are encoded on a separate vector from the viral gag and pol genes, as has been previously described.

Illustrative examples of retroviral-derived env genes which can be employed in the invention include, but are not limited to: MLV envelopes, 10A1 envelope, BAEV, FeLV-B, RD114, SSAV, Ebola, Sendai, FPV (Fowl plague virus), and influenza virus envelopes. Similarly, genes encoding envelopes from RNA viruses (e.g., RNA virus families of Picornaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Birnaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BLV, EBV, CAEV, SNV, ChTLV, STLV, MPMV, SMRV, RAV, FuSV, MH2, AEV, AMV, CT10, EIAV.

In other embodiments, envelope proteins for pseudotyping a virus of present invention include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpesviruses such as Herpes simplex virus types 1 and 2, varicella zoster, cytomegalovirus, Epstein-Bar virus (EBV), human herpesviruses (HHV), human herpesvirus type 6 and 8, Human immunodeficiency virus (HIV), papilloma virus, murine gammaherpesvirus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, any encephaliltis causing virus.

In one embodiment, the invention provides packaging cells which produce recombinant retrovirus, e.g., lentivirus, pseudotyped with the VSV-G glycoprotein.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to CD4+ presenting cells. In a preferred embodiment of the invention, lentiviral envelope proteins are pseudotyped with VSV-G. In one embodiment, the invention provides packaging cells which produce recombinant retrovirus, e.g., lentivirus, pseudotyped with the VSV-G envelope glycoprotein.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles. Any suitable cell line can be employed to prepare packaging cells of the invention. Generally, the cells are mammalian cells. In a particular embodiment, the cells used to produce the packaging cell line are human cells. Suitable cell lines which can be used include, for example, CHO cells, BHK cells, MDCK cells, C3H 10T1/2 cells, FLY cells, Psi-2 cells, BOSC 23 cells, PA317 cells, WEHI cells, COS cells, BSC 1 cells, BSC 40 cells, BMT 10 cells, VERO cells, W138 cells, MRC5 cells, A549 cells, HT1080 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells. In preferred embodiments, the packaging cells are 293 cells, 293T cells, or A549 cells. In another preferred embodiment, the cells are A549 cells.

As used herein, the term "producer cell line" refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:5110-5113. Infectious virus particles may be collected from the packaging cells using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

The delivery of a gene(s) or other polynucleotide sequence using a retroviral or lentiviral vector by means of viral infection rather than by transfection is referred to as "transduction." In one embodiment, retroviral vectors are transduced into a cell through infection and provirus integration. In certain embodiments, a cell is "transduced" if it comprises a gene or other polynucleotide sequence delivered to the cell by infection using a viral or retroviral vector. In particular embodiments, a transduced cell comprises the gene or other polynucleotide sequence delivered by a retroviral or lentiviral vector in its cellular genome.

In particular embodiments, host cells transduced with viral vector of the invention that expresses a therapeutic polypeptide, e.g., a ABCD1 polypeptide, are administered to a subject to treat and/or prevent a disease, disorder, or condition, e.g., adrenoleukodystrophy or adrenomyeloneuropathy. Other methods relating to the use of viral vectors in gene therapy, which may be utilized according to certain embodiments of the present invention, can be found in, e.g., Kay, M. A. (1997) *Chest* 111(6 Supp.):138S-142S; Ferry, N. and Heard, J. M. (1998) *Hum. Gene Ther.* 9:1975-81; Shiratory, Y. et al. (1999) *Liver* 19:265-74; Oka, K. et al. (2000) *Curr. Opin. Lipidol.* 11:179-86; Thule, P. M. and Liu, J. M. (2000) *Gene Ther.* 7:1744-52; Yang, N. S. (1992) *Crit. Rev. Biotechnol.* 12:335-56; Alt, M. (1995) *J. Hepatol.* 23:746-58; Brody, S. L. and Crystal, R. G. (1994) *Ann. N.Y. Acad. Sci.* 716:90-101; Strayer, D. S. (1999) *Expert Opin. Investig. Drugs* 8:2159-2172; Smith-Arica, J. R. and Bartlett, J. S. (2001) *Curr. Cardiol. Rep.* 3:43-49; and Lee, H. C. et al. (2000) *Nature* 408:483-8.

As used herein, unless the context makes clear otherwise, "treatment," "treated," and similar words such as "treating" etc., indicates an approach for obtaining beneficial or desired results, including and preferably clinical results. Treatment can involve optionally either the reduction or amelioration of symptoms of the disease or condition, or the delaying of the progression of the disease or condition.

As used herein, unless the context makes clear otherwise, "prevent," and similar words such as "prevented," "preventing" etc., indicates an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, an "effective amount" or a "therapeutically effective amount" of a transduced host cell or a substance is that amount sufficient to affect a desired biological effect, such as beneficial results, including clinical results.

As used herein "pharmaceutically acceptable carrier" includes any and all solvents, dispersion media, coatings, antibacterial and antifungal agents, isotonic and absorption delaying agents, and the like that are physiologically compatible, including pharmaceutically acceptable cell culture media. In one embodiment, the carrier is suitable for parenteral administration. The carrier can be suitable for intravascular (e.g., intravenous or intraarterial), intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the transduced cells, use thereof in the pharmaceutical compositions of the invention is contemplated.

The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives. As used herein, the terms "include" and "comprise" are used synonymously.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the following description, certain specific details are set forth in order to provide a thorough understanding of various embodiments of the invention. However, one skilled in the art will understand that the invention may be practiced without these details. In addition, it should be understood that the individual vectors, or groups of vectors, derived from the various combinations of the structures and substituents described herein, are disclosed by the present application to the same extent as if each vector or group of vectors was set forth individually. Thus, selection of particular vector structures or particular substituents is within the scope of the present disclosure.

C. Viral Vectors

Retroviral and lentiviral vectors have been tested and found to be suitable delivery vehicles for the stable introduction of genes of interest into the genome of a broad range of target cells. Many vector designs have been optimized for maximum transduction efficiency and transgene expression by including FLAP, RRE, and HPRE or WPRE sequences. In particular, those having ordinary skill in the art often include posttranscriptional regulatory sequences to increase transgene expression. Surprisingly, the present inventors have discovered that inclusion of a WPRE sequence does not significantly increase expression or This configuration results in synthesis of an mRNA transcript whose 5' portion comprises the heterologous nucleic acid coding sequences and whose 3' portion comprises the posttranscriptional regulatory element sequence. In preferred embodiments, vectors of the invention lack or do not comprise a posttranscriptional regulatory element such as a WPRE or HPRE because in some instances these elements increase the risk of cellular transformation and/or do not substantially or significantly increase the amount of mRNA transcript or increase mRNA stability. Therefore, in some embodiments, vectors of the invention lack or do not comprise a WPRE or HPRE as an added safety measure.

The present invention further provides transfer vectors, which may be used to practice methods of the present invention.

While the skilled artisan will appreciate that such transfer vectors may be produced using a variety of different viral vectors, in particular embodiments, the transfer vector is a retroviral vector or a lentiviral vector, in part since lentiviral vectors are capable of providing efficient delivery, integration and long term expression of transgenes into non-dividing cells both in vitro and in vivo. A variety of lentiviral vectors are known in the art, see Naldini et al., (1996a, 1996b, and 1998); Zufferey et al., (1997); Dull et al., 1998, U.S. Pat. Nos. 6,013,516; and 5,994,136, any of which may be adapted to produce a transfer vector of the present invention. In general, these vectors are plasmid-based or virus-based, and are configured to carry the essential sequences for transfer of a nucleic acid encoding a therapeutic polypeptide into a host cell.

The lentiviral genome and the proviral DNA include three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNAs, respectively. Lentiviruses have additional genes including vif, vpr, tat, rev, vpu, nef and vpx. Adjacent to the 5' LTR are sequences necessary for reverse transcription of the genome (the tRNA primer binding site) and for efficient encapsidation of viral. RNA into particles (the Psi site).

In further embodiments, the lentiviral vector is an HIV vector. Thus, the vectors may be derived from human immunodeficiency-1 (HIV-1), human immunodeficiency-2 (HIV-2), simian immunodeficiency virus (SIV), feline immunodeficiency virus (FIV), bovine immunodeficiency virus (BIV), Jembrana Disease Virus (JDV), equine infectious anemia virus (EIAV), caprine arthritis encephalitis virus (CAEV) and the like. HIV based vector backbones (i.e., HIV cis-acting sequence elements and HIV gag, pol and rev genes) are generally be preferred in connection with most aspects of the present invention in that HIV-based constructs are the most efficient at transduction of human cells.

In various embodiments, the vectors of the invention comprise a promoter operably in a microglial cell operably linked to a gene encoding a polypeptide that provides therapy for adrenoleukodystrophies and/or adrenomyeloneuropathies. The vectors may have one or more LTRs, wherein either LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi ('F) packaging signal, RRE), and/or other elements that increase therapeutic gene expression (e.g., poly (A) sequences), except that the vectors of the invention do not comprise a WPRE or HPRE.

In a particular embodiment, the transfer vector of the invention comprises a left (5') retroviral LTR; a central polypurine tract/DNA flap (cPPT/FLAP); a retroviral export element; a promoter active in a microglial cell, operably linked to a polynucleotide encoding an ATP-binding cassette, sub-family D, member 1 (ABCD1) polypeptide; and a right (3') retroviral LTR; wherein the vector does not comprise a woodchuck post-transcriptional regulatory element (WPRE).

In a particular embodiment, the transfer vector of the invention comprises a left (5') retroviral LTR; a retroviral export element; a promoter active in a microglial cell, operably linked to a polynucleotide encoding an ATP-binding cassette, sub-family D, member 1 (ABCD1) polypeptide; a right (3') retroviral LTR; and a poly (A) sequence, wherein the vector does not comprise a woodchuck post-transcriptional regulatory element (WPRE). In another particular embodiment, the invention provides a lentiviral vector comprising: a left (5') LTR; a cPPT/FLAP; an RRE; a MND promoter operably linked to a polynucleotide encoding a human ABCD1 polypeptide (e.g., SEQ ID NO: 1-2); a right (3') LTR; and a polyadenylation sequence; wherein the vector does not comprise a woodchuck post-transcriptional regulatory element (WPRE).

In a certain embodiment, the invention provides a lentiviral vector comprising: a left (5') HIV-1 LTR; a Psi (Ψ) packaging signal; a cPPT/FLAP; an RRE; a MND promoter, operably linked to a cDNA encoding a human ABCD1 polypeptide; a right (3') self-inactivating (SIN) HIV-1 LTR; and a rabbit β-globin polyadenylation sequence; wherein the vector does not comprise a woodchuck post-transcriptional regulatory element (WPRE).

In another embodiment, the invention provides a vector comprising: at least one LTR; a central polypurine tract/DNA flap (cPPT/FLAP); a retroviral export element; and a promoter active in a microglial cell, operably linked to a polynucleotide encoding an ATP-binding cassette, sub-family D, member 1 (ABCD1) polypeptide; wherein the vector does not comprise a woodchuck post-transcriptional regulatory element (WPRE).

In particular embodiment, the present invention provides a vector comprising at least one LTR; a cPPT/FLAP; an RRE; a MND promoter operably linked to a polynucleotide encoding a human ABCD1 polypeptide; and a polyadenylation sequence; wherein the vector does not comprise a woodchuck post-transcriptional regulatory element (WPRE).

In a certain embodiment, the present invention provides at least one SIN HIV-1 LTR; a Psi (Ψ) packaging signal; a cPPT/FLAP; an RRE; a MND promoter, operably linked to a cDNA encoding a human ABCD1 polypeptide; and a rabbit β-globin polyadenylation sequence, wherein the vector does not comprise a woodchuck post-transcriptional regulatory element (WPRE).

The skilled artisan would appreciate that many other different embodiments can be fashioned from the existing embodiments of the invention, such that the therapeutic transgene is expressed in microglial cell in a retroviral vector that lacks a WPRE or HPRE element.

D. Compositions and Formulations

The present invention further includes pharmaceutical compositions comprising transduced cells produced according to methods described herein and a pharmaceutically acceptable carrier. In one embodiment, the carrier is suitable for parenteral administration. The carrier can be suitable for intravenous, intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art.

The compositions of the invention may comprise one or more polypeptides, polynucleotides, vectors comprising same, transduced cells, etc., as described herein, formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., other proteins, polypeptides, small molecules or various pharmaceutically-active agents. There is virtually no limit to other components that may also be included in the compositions, provided that the additional agents do not adversely affect the ability of the composition to deliver the intended gene therapy.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain circumstances it will be desirable to deliver the compositions disclosed herein parenterally, intravenously, intramuscularly, or even intraperitoneally as described, for example, in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington: The Science and Practice of Pharmacy, 20th Edition. Baltimore, Md.: Lippincott Williams & Wilkins, 2000). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, optionally mixing with CPP polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques. The formulations and compositions of the invention may comprise one or more repressors and/or activators comprised of a combination of any number of polypeptides, polynucleotides, and small molecules, as described herein, formulated in pharmaceutically-acceptable or physiologically-acceptable solutions (e.g., culture medium) for administration to a cell or an animal, either alone, or in combination with one or more other modalities of therapy. It will also be understood that, if desired, the compositions of the invention may be administered in combination with other agents as well, such as, e.g., cells, other proteins or polypeptides or various pharmaceutically-active agents.

In a particular embodiment, a formulation or composition according to the present invention comprises a cell contacted with a combination of any number of polypeptides, polynucleotides, and small molecules, as described herein.

In certain aspects, the present invention provides formulations or compositions suitable for the delivery of viral vector systems (i.e., viral-mediated transduction) including, but not limited to, retroviral (e.g., lentiviral) vectors.

Exemplary formulations for ex vivo delivery may also include the use of various transfection agents known in the art, such as calcium phosphate, electroporation, heat shock and various liposome formulations (i.e., lipid-mediated transfection). Liposomes, as described in greater detail below, are lipid bilayers entrapping a fraction of aqueous fluid. DNA spontaneously associates to the external surface of cationic liposomes (by virtue of its charge) and these liposomes will interact with the cell membrane.

In certain aspects, the present invention provides pharmaceutically acceptable compositions which comprise a therapeutically-effective amount of one or more polynucleotides or polypeptides, as described herein, formulated together with one or more pharmaceutically acceptable carriers (additives) and/or diluents (e.g., pharmaceutically acceptable cell culture medium).

Particular embodiments of the invention may comprise other formulations, such as those that are well known in the pharmaceutical art, and are described, for example, in Remington: The Science and Practice of Pharmacy, 20th Edition. Baltimore, Md.: Lippincott Williams & Wilkins, 2000.

E. Gene Therapy Methods

The retroviral vectors provide improved methods of adrenoleukodystrophy and adrenomyeloneuropathy gene therapy. As used herein, the term "gene therapy" refers to the introduction of a gene into a cell's genome. In various embodiments, a viral vector of the invention comprises a promoter that expresses a therapeutic transgene encoding a polypeptide that provides curative, preventative, or ameliorative benefits to a subject diagnosed with or that is suspected of having an adrenoleukodystrophy or adrenomyeloneuropathy. The virus can infect and transduce the cell in vivo, ex vivo, or in vitro. In ex vivo and in vitro embodiments, the transduced cells can then be administered to a subject in need of therapy. The present invention contemplates that the vector systems, viral particles, and transduced cells of the invention are can be use to treat, prevent, and/or ameliorate an adrenoleukodystrophy or adrenomyeloneuropathy in a subject.

In various embodiments, the retroviral vectors are administered by direct injection to a cell, tissue, or organ of a subject in need of gene therapy, in vivo. In various other embodiments, cells are transduced in vitro or ex vivo with vectors of the invention. The transduced cells are then administered to a subject having adrenoleukodystrophy or adrenomyeloneuropathy.

Cells suitable for transduction and administration in the gene therapy methods of the invention include, but are not limited to stem cells, progenitor cells, and differentiated cells. In certain embodiments, the transduced cells are bone marrow stem cells, umbilical cord stem cells, or mesenchymal stem cells.

In various embodiments, the use of stem cells is preferred because they have the ability to differentiate into the appropriate cell types when administered to a particular biological niche, in vivo. The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent. "Self-renewal" refers a cell with a unique capacity to produce unaltered daughter cells and to generate specialized cell types (potency). Self-renewal can be achieved in two ways. Asymmetric cell division produces one daughter cell that is identical to the parental cell and one daughter cell that is different from the parental cell and is a progenitor or differentiated cell. Asymmetric cell division does not increase the number of cells. Symmetric cell division produces two identical daughter cells. "Proliferation" or "expansion" of cells refers to symmetrically dividing cells.

As used herein, the term "pluripotent" means the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. As used herein, the term "multipotent" refers to the ability of an adult stem cell to form multiple cell types of one lineage. For example, hematopoietic stem cells are capable of forming all cells of the blood cell lineage, e.g., lymphoid and myeloid cells.

As used herein, the term "progenitor" or "progenitor cells" refers to cells have the capacity to self-renew and to differentiate into more mature cells. Many progenitor cells differentiate along a single lineage, but may have quite extensive proliferative capacity.

Hematopoietic stem cells (HSCs) give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to the all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). When transplanted into lethally irradiated animals or humans, hematopoietic stem and progenitor cells can repopulate the erythroid, neutrophil-macrophage, megakaryocyte and lymphoid hematopoietic cell pool.

In preferred embodiments, the transduced cells are hematopoeitic stem and/or progentior cells isolated from bone marrow, umbilical cord blood, or peripheral circulation. In particular preferred embodiments, the transduced cells are hematopoeitic stem cells isolated from bone marrow, umbilical cord blood, or peripheral circulation.

Cells of the invention can be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells of the invention are allogeneic.

A "subject," as used herein, includes any animal that exhibits a symptom of an adrenoleukodystrophy or adrenomyeloneuropathy that can be treated with the gene therapy vectors, cell-based therapeutics, and methods disclosed elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by gene therapy.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the term "amount" refers to "an amount effective" or "an effective amount" of a virus or transduced therapeutic cell to achieve a beneficial or desired prophylactic or therapeutic result, including clinical results.

A "prophylactically effective amount" refers to an amount of a virus or transduced therapeutic cell effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a virus or transduced therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient).

In one preferred embodiment, the invention provides transduced cells with the potential to develop into brain microglial cells. In particular embodiments, hematopoietic stem cells are transduced with a vector of the invention and administered to an individual in need of therapy for an adrenoleukodystrophy or adrenomyeloneuropathy. Hematopoietic stem cells are the origin of brain microglial cells and thus, are preferred.

The transduced cells may be administered as part of a bone marrow transplant in an individual that has or has not undergone bone marrow ablative therapy. In one embodiment, transduced cells of the invention are administered in a bone marrow transplant to an individual that has undergone chemoablative or radioablative bone marrow therapy. In preferred embodiments, the subject is a young male.

In one embodiment, a dose of transduced cells is delivered to a subject intravenously. In preferred embodiments, transduced hematopoietic stem cells are intravenously administered to a subject.

In particular embodiments, patients receive a dose of transduced hematopoietic stem cells of about $1 \times 10^5$ cells/kg, about $5 \times 10^5$ cells/kg, about $1 \times 10^6$ cells/kg, about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10^7$ cells/kg, about $5 \times 10^7$ cells/kg, about $1 \times 10^8$ cells/kg, or more in one single intravenous dose. In a certain embodiment, patients receive a dose of transduced hematopoietic stem cells of about $1 \times 10^5$ cells/kg to about $1 \times 10^8$ cells/kg, about $1 \times 10^6$ cells/kg to about $1 \times 10^8$ cells/kg, about $1 \times 10^6$ cells/kg to about $9 \times 10^6$ cells/kg, about $2 \times 10^6$ cells/kg to about $8 \times 10^6$ cells/kg, about $2 \times 10^6$ cells/kg to about $8 \times 10^6$ cells/kg, about $2 \times 10^6$ cells/kg to about $5 \times 10^6$ cells/kg, about $3 \times 10^6$ cells/kg to about $5 \times 10^6$ cells/kg, about $3 \times 10^6$ cells/kg to about $4 \times 10^8$ cells/kg, or any intervening dose of cells/kg.

Transduced cells can be stimulated with cytokines for expansion using existing methods in the art. In various embodiments, subjects are administered 1, 2, 3, 4, 5, or more doses over days, months, or years, as needed to maintain or increase the therapy.

In particular embodiments, hematopoietic stem cells are transduced with a vector of the invention comprising a promoter active in microglial cells, e.g., a MND promoter, that is operably linked to a gene encoding a polypeptide, e.g., ABCD1, that can be used to treat, prevent or ameliorate an adrenoleukodystrophy and/or adrenomyeloneuropathy in a subject.

The present invention now will be described more fully by the following examples. This invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

Example 1

Comparison of Gene Transductions on Normal Human Hematopoietic Stem Cells Using ABCD1 Lentiviral Vectors with or without the WPRE Experimental Overview:

A lentiviral vector comprising a MND promoter operably linked to a cDNA encoding human ACBD1, and a WPRE element (see FIG. 1; CG1711 MND-ALD) vector is not available for commercial development. As a result, Applicants undertook a vector development program to identify an appropriate lentiviral vector to take forward into future clinical trials. The commercially acceptable vector was made as a result of the vector development program and did not alter the ABCD-1 gene operably linked to the MND promoter. Surprisingly, the removal of the WPRE from the vector did not alter the transduction efficiency and transgene expression in human hematopoietic cells. The following series of experiments on hematopoietic cells were performed using short- and long-term progenitor assays to compare two MND-ALD vectors, pLBP100 (see FIG. 1 and SEQ ID NO: 1; WPRE removed) and pLBP140 (see FIG. 1; has functional WPRE), which differed with respect to the presence of WPRE.

Lentiviral Vector Constructs

All lentiviral vectors contained the normal human ATP-binding cassette, sub-family D (ALD), member 1 (ABCD1) cDNA under the control of the MND promoter. FIG. 1 and Table 1 summarizes the different components and their position in the CG1711, pLBP100 and pLBP140 MND-ALD vectors.

TABLE 1

Vector Summary

|  | pLBP100 | pLBP140 |  |
|---|---|---|---|
| HIV Sources | HIV1 (NL4-3) Accession #m19921 | HIV1 (NL4-3) Accession #m19921 |  |
| 5'LTR: |  |  |  |
| Hybrid/WT | WT | WT |  |
| R | + | + |  |
| U5 | + | + |  |

TABLE 1-continued

Vector Summary

|  | pLBP100 | pLBP140 |  |
|---|---|---|---|
| Gag sequences: |  |  |  |
| ORF disrupted | Two stop codons | Two stop codons |  |
| Length | To Nsi I site, 120 bp, longer | To Nsi I site, 120 bp, longer |  |
| RRE and cPPT and S/A | cPPT/CTS RRE (500 bp) | cPPT/CTS RRE (500 bp) | This area of vector uniquely designed by different groups |
| Promoter | MND | MND |  |
| ABCD-1 seq | Nt. 346-2638 | Nt. 346-2638 | Accession no. NM_000033 |
| 5'UT | + | + |  |
| 3'UT | − | + |  |
| WPRE | No | Yes (mutated) |  |
| SIN 3'LTR | + | + | Same deletion |
| Poly A | Synthetic rabbit β-globin poly A (r βgpA) in place of U5 | Synthetic rabbit β-globin poly A (r βgpA) in place of U5 | Synthetic r βgpA adds another degree of self-inactivation by removing most of the LTR nucleotide sequence |

Transduction

Lentiviral pLBP100 and pLBP140 supernatants were produced by calcium phosphate transfection of 293T cells with 5-plasmids (pLBP100 or pLBP140 vectors, HPV 275—gag-pol, ΨN 15—VSV-G env, p633—rev, HPV601—tat). Concentrated pLBP100 was obtained after ultracentrifugation, resuspensed into SCGM (CellGenix Inc., Germany GMBH) medium, and cryopreserved at <−70° C. in single-use cryovials. Infectious titers were determined from flow cytometric analysis of transduced 3T3 cells.

The pLBP100 and pLBP140 lentiviral vector comparison for transduction of human heamtopoietic stem cells was performed among the four separate experiments summarized in Table 2. Procedures and assays for experiments performed are illustrated in FIGS. 2 and 3 respectively.

TABLE 2

Experimental Summary

| Expt. | CD34+ Cell Source | MND-ALD Vector | LV Lot No. | Titer (TU/mL) | MOI | RN | Culture Assays |
|---|---|---|---|---|---|---|---|
| 072010 (BBB6) | Lonza: Fresh BM Lonza: Lot # 0F3668C | pLBP100 pLBP140 | 100701 100717 | $1.3 \times 10^8$ $1.9 \times 10^7$ | 12 8.6 | − − | Liquid and CFC |
| 081010 (BBB8) | AllCells: Fresh mPB Lot# A2186 | pLBP100 pLBP140 | 100701 100724 | $1.3 \times 10^8$ $1.0 \times 10^8$ | 25 25 | − − | Liquid and CFC |
| 091410 (BBB9) | AllCells: Frozen mPB Lot# A2186 | pLBP100 pLBP140 | 100820 100730 | $1.2 \times 10^8$ $1.3 \times 10^8$ | 25 25 | − − | Liquid and CFC |
| 080610 | Lonza: Fresh BM Lonza: Lot # 0F3739B | pLBP100 pLBP140 | 100701 100724 | $1.3 \times 10^8$ $1.0 \times 10^8$ | 25 25 | + + | Liquid, CFC and LTC-IC |

Fresh human bone marrow (BM) CD34+ cells (Lonza, Walkersville, Md.) or fresh or cryopreserved human G-CSF mobilized peripheral blood (mPB) CD34+ cells (AllCells, LLC, Emeryville, Calif.) were washed and cultured for 18 hours in SCGM supplemented with human recombinant IL-3 (60 ng/ml), Flt-3L (100 ng/ml), TPO (100 ng/ml) and SCF (100 ng/ml) (Peprotech) at a cell concentration of $1 \times 10^6$ cells/mL.

Cells were then removed, washed and resuspended in single (expt. 080610) or triplicate (expts. 072010, 081010 and 091410) 200 μL volumes in flat-bottom 96-well well plates at a concentration of $2 \times 10^6$ cells/mL in SCGM (mock control) or pLBP100 or pLBP140) supernatant at MOIs of 8.6 to 25 ($1.7\text{-}5.0 \times 10^7$ TU/ml final titer) supplemented with the same concentrations of cytokines and 8 μg/m protamine sulfate added with virus. In expt. 080610, transduction were performed in 96-well plates pre-coated with 20 μg/mL retronectin (Takara Bio In Shiga, Japan) with overnight incubation at 4° C.

Short-Term Progenitor Assays

At 24 hours after addition of virus, the cells were washed and either (1) resuspended SCGM medium supplemented with the same concentration of cytokines and further incubated over 21 days or (2) 1-cultured in MethoCult H4434 medium (Stem Cell Technologies) for colony forming cells (CFCs).

Total myeloid (CFU-GM) and erythroid (BFU-E) colonies were enumerated at 14 days and the cells suspended in PBS, washed and genomic DNA was prepared with DNEASy kit (QIAGEN) (1-2×10$^6$ viable cells).

Long-Term Culture Initiating Cell (LTC-IC) Assay

Eight 96 well plates were inoculated with the mouse bone marrow stromal cell line MS-5 in Alpha medium supplemented with 10% fetal bovine serum and were gamma-irradiated (30 Gy) when they became nearly confluent.

At two days after irradiation, the pre-established MS-5 stromal layers were inoculated with human CD34+ test cells in 200 µL of StemSpan SFEM (Serum-free Medium, Stem Cell Technologies, Vancouver, Canada) at various dilutions with 16-wells per dilution (2000 cells per well in 16 wells, 1000 cells per well in 16 wells, 500 cells per well in 16 wells, 250 cells per well in 16 wells, 125 cells per well in 16 wells, 62 cells per well in 16 wells, 31 cells per well in 16 wells, 16 cells per well in 16 wells, 8 cells per well in 16 wells). An additional 100,000 CD34+ cells were cultured in bulk for 5 weeks on MS-5 feeder cells. Each week, 100 µL of medium was replaced by 100 µL of fresh StemSpan SFEM. After 5 weeks, the cultures are harvested and the whole contents were then seeded in Methocult™ GF+H4434 (500 µL of methyl cellulose per well of 12 well plates) for 14-day growth of colonies. Individual colonies were then plucked and DNA extracted for subsequent PCR analysis using primers directed at gag sequences in the vector and primers directed at a genomic sequence (Epo gene) in order to have a positive control attesting the presence of genomic DNA after extraction (SOP # GTX/RE/PBM/M-023 and LTGC/RE/PBM/M-07). The frequencies and 95% confidence intervals of LTC-IC were computed using the L-calc software, version 1.1 (Stem Cell Technologies).

Vector Copy Number (VCN) Determination

Average VCN per cell was determined from quantitative (real time) PCR (QPCR) on DNA preparations from either liquid cultures or pooled colony cells in methylcellulose cultures following dilution and washing in PBS. QPCR was performed on the ABI Prism 7000 Sequence Detection System with ABI reagents and 96 well-plates.

Human gag probe and primers used to quantify the vector:

```
GAG-F (forward primer)
5'ggagctagaacgattcgcagtta 3'

GAG-R (reverse primer)
5' ggttgtagctgtcccagtatttgtc 3'

GAG-P (probe, antisense)
5'-(FAM)-acagccttctgatgtctctaaaaggccagg-(TAMRA)-3'
```

Human beta actin probe and primers used to quantify genomic DNA for normalization:

```
Probe:    5' VIC-cctggcctcgctgtccaccttcca-TAMRA

Forward-  5' tccgtgtggatcggcggctcca 3'

Reverse-  5' ctgcttgctgatccacatctg 3'.
```

$\frac{1}{100}^{th}$ of eluted genomic DNA (approximately 50-100 ng) was assayed using 1× TaqMan® Universal Master Mix, 0.72 uM each primer and 0.35 uM probe in a 25 ul reaction with the Absolute Quantification program and default thermal cycling program.

Transgene Expression by Flow Cytometry

The expression of the ABCD1 (ALDP) protein was performed on fixed and permeabilized cells (Fix & Perm Reagents A and B, cat. Nos. GAS001 & GAS002, Invitrogen) using the mouse anti-human ALDP (ABCD1) monoclonal antibody (Clone 1D6, Lot# LV1383343, Chemicon) followed by staining with PE-conjugated rat anti-mouse IgG1 mAb (clone A85-1, BD Pharmingen). The mouse IgG1 monoclonal antibody clone MOPC-21 (BioLegend) was used as an isotype control.

Statistical Analysis

Comparison of group values within each experiment were analyzed using two-tailed non-parametric Mann-Whitney U-test (GraphPad Prism v. 3.0) and where the sample size was sufficient (n=≥3). Significance between the groups was determined at a p value of below 0.05.

Results:

Effects on Progenitor Cell Frequencies

The yield of functional myeloid (CFU-GM) and erythroid (BFU-E) progenitors were compared for all four experiments in FIG. 4 and show no significant effect of adding either pLBP100 or pLBP140 supernatants for triplicate transductions in a first set of experiments (experiments 072010, 081010 and 091410). For the second set of experiments (experiments 080610) in which six sets of methylcellulose cultures for single transductions were compared, a significant increase in myeloid progenitors was observed with addition of pLBP100 while a significant decrease in the yield of erythroid colonies was seen following treatment with pLBP100 and further decreased after pLBP140 transduction.

The frequencies of the more primitive LTC-IC was on average lower after transduction with the two lentiviral vectors (FIG. 5) but as the 95% confidence intervals overlapped then these differences were not significant (p>0.05).

Transduction Efficiency by Vector PCR

Real-time PCR analysis of genomic DNA isolated from cells maintained in liquid culture over 35 days showed a higher estimated vector copy number (VCN) at all time points for pLBP100 as compared with pLBP140 in the second set of experiments (FIG. 6A).

This was also reflected in the higher average VCN for pooled CFCs growing in the methyl cellulose cultures and percent vector positive myeloid colonies from the same experiment (FIGS. 6 B and C). Comparison among the triplicate experiments of the first set of experiments, however, showed no significant difference in VCN of pooled colonies or of the percent colonies tested positive for the vector.

FIG. 7 shows that average VCN and the percent vector positive myeloid colonies decreased following the 5-week LTC-IC for both vector groups with the pLBP100 transduced cells again having the higher VCN (1.1 vs. 0.4 copies) and proportion of positive colonies (51% vs. 35%).

ALDP Transgene Expression by Flow Cytometry

Examples of fluorescence profiles of cells intracellularly stained with the anti-ALDP antibody is shown in the histograms in FIGS. 8A1 and A2 from which the percent positive (determined at beyond 0.5% of the respective mock controls) and the ratio of median fluorescence intensities (MFI) was determined and presented in FIGS. 8B and C. The level of transgene expression varied among the experiments with a higher average percent of expressing cells occurring for the pLBP100 as compared to pLBP140 groups in expts. 072010 and 080610. However the opposite was observed in expt. 091410 and comparable levels in expt. 081010. Statistical comparisons among the triplicate experiments showed no significant differences in either the percent ALDP+ cells or the MFI (p>0.05).

CONCLUSIONS

Comparisons among four separate experiments using two preparations of the preclinical pLBP100 lentiviral vector and three preparations of the WPRE containing pLBP140 vector and involving transductions of normal human CD34+ cells originating from bone marrow or GCSF-mobilized peripheral blood was performed. With the exception of an increase in myeloid and a decrease in erythroid progenitors in experiment 080610 there was no significant toxicity of the supernatants, either for early progenitors or the more primitive LTC-ICs. There was a tendency for lower transduction efficiencies for the pLBP140 according to average VCN or proportion of vector containing myeloid colonies or LTC-IC but this was not statistically significant for those experiments of sufficient sample size (n=3). The level of transgene expression given by the two vectors produced mixed results with two experiments showing a higher percent of ALDP+ cells from pLBP100 and one experiment showing a lower percent as compared to pLBP140. These differences were not statistically significant.

Overall, there appears to be no advantage of adding the WPRE to the MND-ALD vector. Thus, vectors of the present invention provide increased safety and equal of superior efficacy compared to WPRE containing vectors. Moreover, the results show that vectors of the invention are well suited for further development and clinical application.

Example 2

Evaluation of Functional Correction of ALD Protein Deficiency in ALD-Defective Primary Human Fibroblasts Experimental Overview The accumulation of very long chain fatty acids (VLCFA), particularly the C26 chain, is often referred to as the biochemical "hallmark" of ALD. Hubbard, *Mol Genet. Metab.* 97:212-220 (2009). Transduction of defective cells with retroviral vectors containing the ABCD1 cDNA restores functional ALD protein (ALDP) levels and results in decreased level of VLCFAs. This has been shown in different cell populations including primary fibroblast lines from ALD patients.

The C26:0 lyso-PC assay (LPC assay), developed at the Kennedy Krieger Institute (Baltimore, Md.), measures VLCFA by liquid chromatography and tandem mass spectrophotometry. This method was developed for newborn blood spots and was also validated on plasma and cultured skin fibroblasts. In this example, the C26:0 lyso-PC assay was used to demonstrate the functional correction of the biochemical defect in ALD patient fibroblasts. The purpose of this experiment was to compare the efficacy of the vectors pLBP100 (p100) and pLBP140 (p140) in reducing VLCFA levels in vector-modified ALD-defective fibroblast cells.

Cell Lines

Primary human fibroblast cells GM04496 and AG01440 were obtained from the Coriell Cell Repository (Camden, N.J., USA). The GM04496 cells are un-transformed human fibroblasts isolated from an ALD-negative patient with an unknown mutation of the ABCD1 gene. AG01440 cells are normal human fibroblasts. Cells were grown in DMEM (GIBCO Life Technologies, Carlsbad, Calif.) with 15% FBS (HyClone FBS, GIBCO Life Technologies) at 37° C., 5% $CO_2$ in a humidified incubator.

TF-1 cells (ATCC® Number CRL-2003™) are a human lymphoblast line derived from a bone marrow erythroleukemia. Cells were grown in RPMI-1640 (GIBCO Life Technologies) with 10% FBS.

293T cells (Stanford University) which are used to produce lentiviral vectors, were grown in DMEM with 10% FBS.

Transduction Protocol and Plating for Lyso-PC Assay

Sub-confluent cells were transduced with viral supernatant in media+8 ug/ml polybrene (Hexadimethrine Bromide, Sigma, St Louis Mo.) for 14-16 hrs. Fresh medium was replaced on the following day. As early as 3 days post-transduction, the majority of cells were plated in triplicate in 12-well plates (2 replicates for lipid extraction and one for protein analysis. (Falcon #35-3043). An equivalent number of normal-control cells (293T, AG01440 or TF-1 were also plated or pelleted. Cell monolayers were washed twice with 1×HBSS buffer (GIBCO Life Technologies) and frozen in situ at −20° C. The freezing method was tested first at Kennedy Krieger and determined to be comparable to harvest of fresh cell monolayers. The remaining cells were kept in culture.

Genomic DNA Isolation and Vector Copy Number (VCN) Determination

The cells remaining after plating for LPC assay were kept in culture for genomic DNA harvest until at least day 9 post transduction for DNA isolation and VCN analysis. Lipid and Protein extraction was completed at the Kennedy Krieger Institute.

Results:

Lyso-PC Analyses of 4496 Cells and Various Normal and Negative Controls

The 4496 cells and normal-fibroblast 1440 cells were plated for analysis. ALDP was detectable in TF-1 cells and 293 cells by immunostaining and flow cytometry. Thus, these cells were also assayed as alternative positive (i.e., normal ALDP-phenotype) controls for baseline levels of C26:0 LPC. Samples were assayed in four independent analyses.

The baseline levels of C26:0LPC ranged from 3-50 pmol/mg protein in cells with a normal phenotype, and the 4496 cells had elevated levels in each analysis. Overall, there was at least a 5-fold difference (ratio below 0.2) in the levels of C26:0LPC in normal cells compared to 4496. This ratio was similar to the results reported for the patient blood spots.

Comparison of 4496 Cells Transduced with p100 and p140

4496 cells were transduced with p100 and p140. Cells were analyzed for VLCFA and VCN as described herein. The LysoPC assay results are shown in Table 3. The duplicate wells are averaged and normalized to the mock transduced cells. The ratio of VLCFA correction to mock versus VCN is shown in FIG. 10. As VCN decreases to ≤1 copy, the cell population is expected to be mixture of untransduced cells and cells with 1 or 2 vector-copies per cell; therefore VLCFA is expected to decrease (FIG. 10).

TABLE 3

C26:0LPC results in 4496 cells transduced with Lenti-D p100 and LVVp140

|  | MOI | Total pmolesC26:0LPC/mg protein (replicate wells) |  | Average of replicate wells | ratio to mock txd |
|---|---|---|---|---|---|
| Mock txd 4496 |  | 50.53 | 58.94 | 54.73 | 1.00 |
| Lenti-D | 3 | 8.82 | 8.47 | 8.65 | 0.16 |
| p100 | 1 | 11.05 | 12.57 | 11.81 | 0.21 |
|  | 0.3 | 20.59 | 25.57 | 23.08 | 0.42 |
| p140 | 3 | 15.55 | 10.81 | 13.18 | 0.24 |
|  | 1 | 10.35 | 15.37 | 12.86 | 0.23 |
|  | 0.3 | 22.74 | 33.34 | 28.04 | 0.51 |
| Normal 293T |  | 6.98 | 6.75 | 6.87 | 0.12 |

The ratio of 0.2 was established as the level of cells with a normal phenotype compared to mock-txd 4496 cells. VLCFA accumulation in 4496 cells is corrected to the level of normal cells for both vectors when VCN≥~1.5. The trend for a decrease in correction is present with both vectors at VCN 1.0-0.6.

CONCLUSIONS

The C26:0 lyso-PC assay performed at the Kennedy Krieger Institute (Hubbard 2009), measured VLCFA by the liquid chromatography and tandem mass spectrophotometric method, confirmed the biochemical defect in ALD-patient cell line GM04496 cells of accumulation of C26. After transduction with p100 and p140, cells were positive for ALDP expression, as demonstrated by flow cytometry (data not shown) and cells with average VCN≥1.5 showed complete correction of VLCFA accumulation to the level of cells with a normal phenotype. Equivalent results were obtained when cells transduced with p100 and p140 were compared, supporting the effectiveness of p100, which lacks the WPRE sequences.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:
1. A method of gene therapy comprising intravenously administering to a subject having adrenoleukodystrophy or adrenomyeloneuropathy, one or more CD34+ hematopoietic stem or progenitor cells comprising a vector selected from the group consisting of:
  a) a vector comprising from 5' to 3':
    (i) a left (5') retroviral LTR;
    (ii) a central polypurine tract/DNA flap (cPPT/FLAP);
    (iii) a retroviral export element;
    (iv) a promoter active in a microglial cell, operably linked to a polynucleotide encoding an ATP-binding cassette, sub-family D, member 1 (ABCD1) polypeptide; and
    (v) a right (3') retroviral LTR;
    wherein the vector does not comprise a post-transcriptional regulatory element;
  b) a lentiviral vector comprising from 5' to 3':
    (i) a left (5') LTR;
    (ii) a cPPT/FLAP;
    (iii) an RRE;
    (iv) a MND promoter operably linked to a polynucleotide encoding a human ABCD1 polypeptide;
    (v) a right (3') LTR; and
    (vi) a polyadenylation sequence;
    wherein the vector does not comprise a post-transcriptional regulatory element;
  c) a lentiviral vector comprising from 5' to 3':
    (i) a left (5') HIV-1 LTR;
    (ii) a Psi (Ψ) packaging signal;
    (iii) a cPPT/FLAP;
    (iv) an RRE;
    (v) a MND promoter, operably linked to a cDNA encoding a human ABCD1 polypeptide;
    (vi) a right (3') self-inactivating (SIN) HIV-1 LTR; and
    (vii) a rabbit β-globin polyadenylation sequence;
    wherein the vector does not comprise a post-transcriptional regulatory element;
  d) a vector comprising from 5' to 3':
    (i) a left (5') retroviral LTR;
    (ii) a central polypurine tract/DNA flap (cPPT/FLAP);
    (iii) a retroviral export element;
    (iv) a promoter active in a microglial cell, operably linked to a polynucleotide encoding an ATP-binding cassette, sub-family D, member 1 (ABCD1) polypeptide;
    (v) a right (3') retroviral LTR;
    (vi) a polyadenylation (polyA) sequence; and
    wherein the vector does not comprise a post-transcriptional regulatory element; and
  e) a lentiviral vector comprising from 5' to 3':
    (i) a left (5') HIV-1 LTR;
    (ii) a Psi (Ψ) packaging signal;
    (iii) a cPPT/FLAP;
    (iv) an RRE;
    (v) a MND promoter, operably linked to a cDNA encoding a human ABCD1 polypeptide;
    (vi) a right (3') self-inactivating (SIN) HIV-1 LTR; and
    (vii) a polyadenylation (polyA) sequence;
    wherein the vector does not comprise a post-transcriptional regulatory element;
  wherein the gene therapy treats adrenoleukodystrophy or adrenomyeloneuropathy in the subject.

2. A method of treating adrenoleukodystrophy or adrenomyeloneuropathy, comprising intravenously administering to a subject one or more CD34+ hematopoietic stem or progenitor cells transduced with a vector selected from the group consisting of:
  a) a vector comprising from 5' to 3':
    (i) a left (5') retroviral LTR;
    (ii) a central polypurine tract/DNA flap (cPPT/FLAP);
    (iii) a retroviral export element;
    (iv) a promoter active in a microglial cell, operably linked to a polynucleotide encoding an ATP-binding cassette, sub-family D, member 1 (ABCD1) polypeptide; and
    (v) a right (3') retroviral LTR;
    wherein the vector does not comprise a post-transcriptional regulatory element;
  b) a lentiviral vector comprising from 5' to 3':
    (i) a left (5') LTR;
    (ii) a cPPT/FLAP;
    (iii) an RRE;
    (iv) a MND promoter operably linked to a polynucleotide encoding a human ABCD1 polypeptide;
    (v) a right (3') LTR; and
    (vi) a polyadenylation sequence;
    wherein the vector does not comprise a post-transcriptional regulatory element;
  c) a lentiviral vector comprising from 5' to 3':
    (i) a left (5') HIV-1 LTR;
    (ii) a Psi (Ψ) packaging signal;
    (iii) a cPPT/FLAP;
    (iv) an RRE;
    (v) a MND promoter, operably linked to a cDNA encoding a human ABCD1 polypeptide;
    (vi) a right (3') self-inactivating (SIN) HIV-1 LTR; and
    (vii) a rabbit β-globin polyadenylation sequence;
    wherein the vector does not comprise a post-transcriptional regulatory element;
  d) a vector comprising from 5' to 3':
    (i) a left (5') retroviral LTR;
    (ii) a central polypurine tract/DNA flap (cPPT/FLAP);
    (iii) a retroviral export element;
    (iv) a promoter active in a microglial cell, operably linked to a polynucleotide encoding an ATP-binding cassette, sub-family D, member 1 (ABCD1) polypeptide;
    (v) a right (3') retroviral LTR;
    (vi) a polyadenylation (polyA) sequence; and
    wherein the vector does not comprise a post-transcriptional regulatory element; and
  e) a lentiviral vector comprising from 5' to 3':
    (i) a left (5') HIV-1 LTR;
    (ii) a Psi (Ψ) packaging signal;
    (iii) a cPPT/FLAP;
    (iv) an RRE;
    (v) a MND promoter, operably linked to a cDNA encoding a human ABCD1 polypeptide;
    (vi) a right (3') self-inactivating (SIN) HIV-1 LTR; and
    (vii) a polyadenylation (polyA) sequence;
  wherein the vector does not comprise a post-transcriptional regulatory element;
  wherein the treatment reduces or ameliorates of symptoms of adrenoleukodystrophy or adrenomyeloneuropathy in the subject, or the delays progression of adrenoleukodystrophy or adrenomyeloneuropathy in the subject.

3. The method of claim 1 or claim 2, wherein the one or more CD34+ hematopoietic stem or progenitor cells are CD34+ hematopoietic stem cells.

4. The method of claim 3, wherein the CD34+ hematopoietic stem cells are isolated from bone marrow, umbilical cord blood, or peripheral blood.

5. The method of claim 1 or claim 2, wherein the subject has undergone chemoablative or radioablative bone marrow therapy.

6. The method of claim 1 or claim 2, wherein the subject is a young male.

7. The method of claim 6, wherein the young male is between 3 to 15 years of age.

8. The method of claim 1 or claim 2, wherein, in the vector, the promoter of the left (5') LTR, the left (5') retroviral LTR, or left (5') HIV-1 LTR is replaced with a heterologous promoter selected from the group consisting of: a cytomegalovirus (CMV) promoter, a Rous Sarcoma Virus (RSV) promoter, or an Simian Virus 40 (SV40) promoter.

9. The method of claim 1 or claim 2, wherein, in the vector, the right (3') LTR or the right (3') retroviral LTR is a self-inactivating (SIN) LTR.

10. The method of claim 8, wherein, in the vector, the right (3') LTR or the right (3') retroviral LTR is a self-inactivating (SIN) LTR.

11. The method of claim 1 or claim 2, wherein, in the vector, the promoter active in a microglial cell comprises a myeloproliferative sarcoma virus enhancer, negative control region deleted, dl587rev primer-binding site substituted (MND) promoter or transcriptionally active fragment thereof.

12. The method of claim 1 or claim 2, wherein, in the vector, the polynucleotide encoding the ABCD1 polypeptide is a cDNA.

13. The method of claim 1 or claim 2, wherein, in the vector, the cDNA comprises an optimized Kozak sequence.

14. The method of claim 1 or claim 2, wherein, in the vector, the polyadenylation sequence is a bovine growth hormone polyadenylation signal or a rabbit β-globin polyadenylation sequence.

* * * * *

UNITED STATES PATENT AND TRADEMARK OFFICE
CERTIFICATE OF CORRECTION

PATENT NO. : 9,789,139 B2
APPLICATION NO. : 14/125220
DATED : October 17, 2017
INVENTOR(S) : Maria Joann Denaro et al.

It is certified that error appears in the above-identified patent and that said Letters Patent is hereby corrected as shown below:

On the Title Page

"(86) PCT No.: PCT/US2012/041639"
Should read:
--(86) PCT No.: PCT/US2012/041693--

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*